United States Patent
Park et al.

(10) Patent No.: US 9,631,020 B2
(45) Date of Patent: *Apr. 25, 2017

(54) ANTI-C-MET ANTIBODY HAVING HGF ACTIVITY AND USE THEREOF

(75) Inventors: Young Woo Park, Daejeon (KR); Ki Won Jo, Daejeon (KR); Chan Woong Park, Daejeon (KR); Seok Ho Yoo, Daejeon (KR); Myeoung Hee Jang, Daejeon (KR); Hye Nan Kim, Daejeon (KR); Seon Ha Yun, Daejeon (KR); Kyu Won Cho, Daejeon (KR); Mi Ra Park, Daejeon (KR)

(73) Assignees: Korea Research Institute of Bioscience and Biotechnology, Daejeon (KR); Y-Biologics Inc., Daejeon (KR)

( * ) Notice: Subject to any disclaimer, the term of this patent is extended or adjusted under 35 U.S.C. 154(b) by 642 days.

This patent is subject to a terminal disclaimer.

(21) Appl. No.: 14/123,533

(22) PCT Filed: Jun. 4, 2012

(86) PCT No.: PCT/KR2012/004395
§ 371 (c)(1),
(2), (4) Date: Mar. 5, 2014

(87) PCT Pub. No.: WO2012/165925
PCT Pub. Date: Dec. 6, 2012

(65) Prior Publication Data
US 2014/0193431 A1    Jul. 10, 2014

(30) Foreign Application Priority Data
Jun. 3, 2011    (KR) .................. 10-2011-0054177

(51) Int. Cl.
*C07K 16/28* (2006.01)
*A61K 39/00* (2006.01)

(52) U.S. Cl.
CPC .... *C07K 16/2863* (2013.01); *A61K 2039/505* (2013.01); *C07K 2317/21* (2013.01); *C07K 2317/622* (2013.01); *C07K 2317/75* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 7,498,420 | B2 | 3/2009 | Michaud et al. |
| 2010/0115639 | A1 | 5/2010 | Goetsch |
| 2012/0149031 | A1 | 6/2012 | Goetsch et al. |

FOREIGN PATENT DOCUMENTS

EP    2287197    2/2011

OTHER PUBLICATIONS

Translation Dated Nov. 26, 2014 of Notice of Allowance Dated Sep. 4, 2014 From the Korean Intellectual Property Office Re. Application No. 10-2011-0054177.
International Search Report and the Written Opinion Dated Dec. 3, 2012 From the Korean Intellectual Property Office Re. Application No. PCT/KR2012/0004395.
Kolar et al. "Immunoglobulin Mu Heavy Chain [*Homo sapiens*]", GenBank: AAV39919.1, GenBank Accession No. AAV39919, Jun. 7, 2007.
Su et al. "Immunoglobulin Lambda-1 Variable Region [*Homo sapiens*]", GenBank: CAE18207.1, GenBank Accession No. CAE18207, Feb. 23, 2004.
Notice of Allowance Dated Sep. 4, 2014 From the Korean Intellectual Property Office Re. Application No. 10-2011-0054177.
Prat et al. "Agonistic Monoclonal Antibodies Against the Met Receptor Dissect the Biological Responses to HGF", Journal of Cell Science, 111: 237-247, Dec. 23, 1997.

*Primary Examiner* — Sharon Wen

(57) ABSTRACT

Disclosed are a human antibody comprising a human complementarity-determining region (CDR), which binds specifically to c-Met, and a framework region (FR), a polynucleotide encoding the human antibody, an expression vector comprising the polynucleotide, a transformant transformed with the expression vector, a method of producing the human antibody B7 by culturing the transformant, a wound healing composition comprising the human antibody as an active ingredient, a cell regeneration composition comprising the antibody as an active ingredient, and a drug conjugate comprising a drug linked to the human antibody. The c-Met-specific human antibody can function as an HGF mimic that can be used as a wound healing composition. The antibody can be widely used to determine the treatment and prognosis of various diseases, including neuronal infarction, progressive nephropathy, liver cirrhosis, lung fibrosis, kidney injury, liver injury, lung injury, and ulcerative wounds, which are treated by activation of HGF or c-Met.

20 Claims, 14 Drawing Sheets

Bst NI-Digestion (in 8% Acrylamide gel)

1-1st non-reducing
2-3rd non-reducing
3-1st reducing
4-2nd reducing
5-3rd reducing
6-4th reducing
7-5th reducing

ANTI-C-MET ANTIBODY HAVING HGF ACTIVITY AND USE THEREOF

RELATED APPLICATIONS

This application is a National Phase of PCT Patent Application No. PCT/KR2012/004395 having International filing date of Jun. 4, 2012, which claims the benefit of priority of Korean Patent Application No. 10-2011-0054177 filed on Jun. 3, 2011. The contents of the above applications are all incorporated by reference as if fully set forth herein in their entirety.

SEQUENCE LISTING STATEMENT

The ASCII file, entitled 58153SequenceListing.txt, created on Dec. 2, 2013, comprising 12,499 bytes, submitted concurrently with the filing of this application is incorporated herein by reference.

TECHNICAL FIELD

The present invention relates to a c-Met-specific human antibody having HGF activity, and more particularly to a human antibody comprising a human complementarity-determining region (CDR), which binds specifically to c-Met, and a framework region (FR), a polynucleotide encoding the human antibody, an expression vector comprising the polynucleotide, a transformant transformed with the expression vector, a method of producing the human antibody B7 by culturing the transformant, a wound healing composition comprising the human antibody as an active ingredient, a cell regeneration composition comprising the human antibody as an active ingredient, and a drug conjugate comprising a drug linked to the human antibody.

BACKGROUND ART

Hepatocyte Growth factor/scattering factor (HGF/SF) is a pleiotropic cytokine that performs various functions in developmental processes. HGF/SF binds to its receptor Met tyrosine kinase to induce various bioreactions, including the migration, invasion, proliferation, survival and morphological change of target cells (Jiang et al., Critical Reviews in Oncology/Hematology. 53:35-69, 2005). HGF/SF is a cytokine of mesenchymal origin and was reported to act on hepatocytes and other epithelial cells, including endothelial cells, melanocytes, hematopoietic cells and osteocytes, to activate the above reactions through its receptor Met (Tamagnone and Comoglio, Cytokine & Growth factor Rev. 8:129-142, 1997).

The present inventors previously reported that the deregulation of HGF/SF-Met signaling does not influence the usual function of hepatocytes, but adversely affects the regeneration of damaged hepatocytes. Since then, the present inventors confirmed that, when the skin in addition to the liver is damaged, HGF/SF and c-Met are secreted. In other words, large amounts of HGF/SF and c-Met are secreted from hyperproliferative skin tissue to promote the proliferation of skin cells. However, it was reported that c-Met is found in the skin and hair follicles, whereas HGF/SF is usually expressed only in hair follicles and is found in damaged skin. Thus, HGF/SF remains in an inactivated state until the skin is damaged, and it is activated around wounds after the skin is damaged (Journal of Cell Biology 177(1):151-162, 2007). Accordingly, it is known that HGF/c-Met directly regulate skin regeneration and repair (Nakamura et al., Nature. 342:440-443, 1993; Huh et al., Proc Natl Acad Sci USA. 101:4477-4482, 2004).

In vivo and laboratory studies indicated that HGF/SF also acts on the nervous system, and many studies on the function of HGF/SF to protect motor neurons were reported (Novak et al., Journal of Neuroscience. 20:326-337, 2000). In addition, it was suggested that HGF/SF plays an important role in defensive physiological mechanisms following general organ damage such as heart damage (Nakamura et al., J Clin Invest. 106:1511-1519, 2000). Indeed, it was demonstrated that the HGF/MET pathway is involved in the processes of cardiac infraction, progressive nephritis, liver cirrhosis and pulmonary fibrosis and that HGF is overexpressed in lesions of such degenerative diseases to exhibit a physiological activity of protecting tissue from damage (Comoglio et al., Nature Review Drug Discovery. 7:504-516, 2008).

Therefore, it has been suggested that HGF/SF can be developed as an agent for preventing the death of neural cells in the central nervous system, and an agent for treating neurodegenerative diseases, including Parkinson's disease, ischemia leading to nervous infarction, and also regenerative therapeutic agents that are used after the occurrence of damage to the heart, the kidneys, the liver and the lungs, as well as ulcerative wounds.

The excessive activity of HGF/c-Met signaling is associated with tumorigenesis of various endothelial cells and angiogenesis, and from this point of view, it was suggested that an antagonistic c-Met antibody that targets c-Met can be used as an anticancer agent (Comoglio et al., Nature Review Drug Discovery. 7:504-516, 2008). For example, it was reported that a one-armed c-Met antibody efficiently inhibits tumor growth in a transplanted mouse model by negatively regulating the activation of HGF caused by dimerization of c-Met (Jin et al, Cancer Research 68(11): 4360-4368, 2008; Comoglio et al., Nature Review Drug Discovery. 7:504-516, 2008). In addition, in T-cell therapy, an antibody to an antigen that is overexpressed in cancer cells is used in tumor targeting for linking of T cells in the genetic manipulation of T cells that selectively recognizes a cancer cell surface antigen (Sadelain, The Cancer Journal 15(6):451-455, 2009).

DISCLOSURE

Technical Problem

The present inventors have made extensive efforts to develop an antibody that exhibits various physiological activities while targeting c-Met, and as a result, have found that a human antibody B7 comprising a human complementarity-determining region (CDR), which binds specifically to c-Met so as to target c-Met, and a framework region (FR), can show activity similar to HGF and function as an agonist antibody that binds to the cell surface molecule c-Met to induce signaling, thereby completing the present invention.

Technical Solution

It is an object of the present invention to provide a human antibody comprising: a human complementarity-determining region that binds specifically to c-Met; and a framework region (FR).

Another object of the present invention is to provide a polynucleotide encoding the heavy-chain variable region and light-chain variable region of the human antibody.

Still another object of the present invention is to provide an expression vector comprising: a polynucleotide encoding the heavy-chain variable region; and a polynucleotide encoding the light-chain variable region.

Still another object of the present invention is to provide a transformant transformed with the expression vector.

Still another object of the present invention is to provide a method of producing the human antibody B7 by culturing the transformant.

Still another object of the present invention is to provide a wound healing composition comprising the human antibody as an active ingredient.

Still another object of the present invention is to provide a cell regenerating composition comprising the human antibody as an active ingredient.

Still another object of the present invention is to provide a wound healing method comprising administering a pharmaceutically effectively amount of the human antibody to a subject.

Still another object of the present invention is to provide a composition for treating neurodegenerative disease, comprising the human antibody as an active ingredient.

Still another object of the present invention is to provide a composition for treating ulcerative damage to an organ, the composition comprising the human antibody as an active ingredient.

Still another object of the present invention is to provide a drug conjugate comprising a drug linked to the human antibody.

Advantageous Effects

The c-Met-specific human antibody according to the present invention can act as an HGF mimic, and thus can be used as an active ingredient for a wound healing composition. In addition, it can be widely used to determine the treatment and prognosis of various diseases, including neuronal infarction, progressive nephropathy, liver cirrhosis, lung fibrosis, kidney injury, liver injury, lung injury, and ulcerative wounds, which are treated by the activation of HGF or c-Met.

BEST MODE

Figure 1:
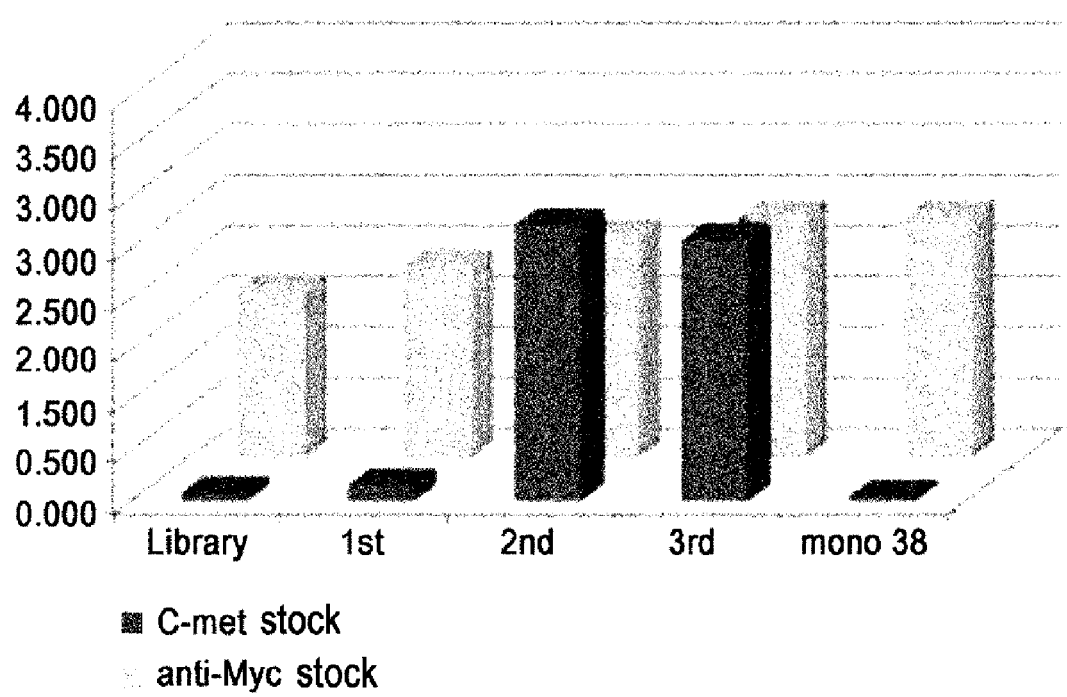
FIG. 1 is a graphic diagram showing the results of ELISA for c-Met polyclonal phage antibodies.

To achieve the above-described objects, in one aspect, the present invention provides a human antibody comprising: a human complementarity-determining region (CDR) that binds specifically to c-Met; and a framework region (FR).

As used herein, the term "c-Met" refers to a receptor of HGF (hepatocyte growth factor) and is used interchangeably with the term "Met" or "Met receptor". For the purposes of the present invention, c-Met is used as a target to which the human antibody according to the present invention specifically binds, but is not limited thereto.

As used herein, the term "complementarity-determining region (CDR)" means a ring-shaped region that constitutes the variable region of the antibody and that is involved in the recognition of an antigen. The sequence of CDR determines the specificity of the antibody to the antigen.

As used herein, the term "framework region (FR)" refers to a region that constitutes the variable region of the antibody and that is located between the CDRs to function to support the ring structure of the CDR.

As used herein, the term "variable region" refers to a portion that binds specifically to the antigen while showing many variations in its sequence. The variable region generally includes CDR and FR.

As used herein, the term "human antibody" means, in a broad sense, an antibody comprising a variable region (CDR and FR) derived from human immunoglobulin, and means, in a narrow sense, an antibody comprising the variable region and constant region derived from human immunoglobulin. The human antibody may include not only a whole antibody but also a functional fragment of the antibody molecule. The whole antibody comprises two full length light chains and two full length heavy chains. Each light chain is linked to the heavy chain by a disulfide bond. Preferably, the human antibody may be a monoclonal antibody. In addition, the functional fragment of the antibody means a fragment having an antigen-binding function and may include Fab, Fab', F(ab')2, Fv, double-stranded Fv(dsFv) and the like. Among the antibody fragments, Fab has light-chain and heavy-chain variable regions, a light-chain constant region and a first heavy-chain constant region (CH1) and may include one antigen binding region; Fab' can be distinguished from Fab in that it includes a hinge region including one or more cysteine residues at the C-terminal end of the heavy-chain CH1 domain; and the F(ab')2 antibody can be distinguished from other fragments in that cysteine residues in the hinge region of Fab' form a disulfide bond. Meanwhile, Fv means a minimal antibody fragment having only a heavy-chain variable region and a light-chain variable region and is generally classified into single-stranded Fv (scFv) and double-stranded Fv (dsFv). The single-stranded Fv (scFv) may have a configuration in which the heavy-chain variable region is covalently linked to the light-chain variable region by a peptide linker, and the double-stranded Fv (dsFv) may have a configuration in which the heavy-chain variable region is linked to the light-chain variable region by a disulfide bond. These functional fragments can be produced using various methods. Generally, these fragments can be produced by enzymatically hydrolyzing antibody proteins. For example, Fab can be obtained by cleaving the whole antibody with papain, and F(ab')2 can be obtained by cleaving the whole antibody with pepsin. Preferably, these antibody fragments can be produced by gene recombination techniques known in the art (WO 88/10649, WO 88/106630, WO88/07085, WO 88/07086 and WO 88/09344). Because all the elements of the human antibody are of human origin, the human antibody has a low possibility of causing an immune reaction compared to conventional humanized antibodies or mouse antibodies. Thus, when the human antibody is administered to humans, it will not cause an undesired immune response, suggesting that it is highly useful as a therapeutic antibody for humans. For the purpose of the present invention, the human antibody can be regarded as a human antibody that binds specifically to c-Met. Further, the human antibody will function as an HGF mimic that induces HGF/c-Met signaling and binds specifically to c-Met, suggesting that the human antibody acts as an agonist antibody. However, the function of the human antibody is not limited to the above functions.

As used herein, the term "monoclonal antibody" refers to a protein molecule that is directed against and binds specifically to a single antigenic site. The monoclonal antibody can be secreted and produced from hybridoma cells prepared by a fusion method well known in the art (Kohler et al., European Journal of Immunology 6; 511-519). The hybridoma cells are prepared by fusing a cancer cell line with immune cells from an immunologically suitable host animal such as a mouse injected with antigen protein. This cell fusion can be performed using, for example, polyethylene glycol, according to a method known in the art, and the fused hybridoma cells can be proliferated by a standard culture method. For example, a uniform cell population can be obtained by performing sub-cloning using a limited dilution method, after which a large amount of hybridoma cells capable of producing an antibody specific to an antigen can be cultured in vitro or in vivo.

The human antibody that is provided according to the present invention may preferably comprise: a heavy-chain variable region comprising a heavy-chain CDR1 set forth in SEQ ID NO: 1, a heavy-chain CDR2 set forth in SEQ ID NO: 2, and a heavy-chain CDR3 set forth in SEQ ID NO: 3; and a light-chain variable region comprising a light-chain CDR1 set forth in SEQ ID NO: 4, a light-chain CDR2 set forth in SEQ ID NO: 5, and a light-chain CDR3 set forth in SEQ ID NO: 6. Most preferably, the human antibody according to the present invention may comprises a heavy-chain variable region amino acid sequence set forth in SEQ ID NO: 7 and a light-chain variable region amino acid region set forth in SEQ ID NO: 8. The heavy-chain variable region amino acid sequence may be encoded by a polynucleotide sequence of SEQ ID NO: 9, and the light-chain variable region amino acid region may be encoded by a polynucleotide sequence of SEQ ID NO: 10.

In addition, the human antibody may be glycosylated and/or PEGylated in order to increase its retention time in the body after administration, but is not limited thereto.

As used herein, the term "glycosylation" refers to a process that introduces a glycosyl group into a protein. The glycosylation is performed by linking a glycosyl group to the serine, threonine, asparagine or hydroxylysine residue of a target protein by glycosyl transferase. The glycosylated protein can be used to constitute biological tissue and plays an important role in recognizing cells on the cell surface. Thus, in the present invention, the effect of the human antibody can be improved by glycosylating the human antibody or changing the pattern of the glycosylation.

As used herein, the term "PEGylation" refers to a process that increases the blood retention time of the human antibody by introducing polyethylene glycol into the human antibody (Anna M. Wu, et al., Nature Biotechnology, 23(9): 1137-1146, 2005; David Schrama, et al., Drug Discovery, 5:147-159, 2006; Alain Beck, et al., Immunology, 10:345-352, 2010). Specifically, by PEGylating polymer nanoparticles with polyethylene glycol, the hydrophilicity of the surface of the nanoparticles can be increased, and rapid degradation of the nanoparticles in the body can be prevented by the so-called stealth effect that prevents the nanoparticles from being recognized by immune-functional cells, including human macrophages that eat and digest effete matter and foreign matter. Thus, the PEGylation can increase the blood retention time of the human antibody. The PEGylation that is used in the present invention can be performed by forming an amide group by the bonding between the carboxyl group of hyaluronic acid and the amine group of polyethylene glycol. However, the PEGylation is not limited thereto, and may be performed in various manners. Polyethylene glycol that is used in the present invention is not specifically limited, but preferably a molecular weight of 100-1,000 and a linear or branched-chain structure.

In the glycosylation and/or PEGylation process, various glycosylation and/or PEGylation patterns known in the art may be applied as long as the function of the inventive antibody is maintained. The scope of the human antibody of the present invention includes all human antibodies having various glycosylation and/or PEGylation patterns.

In an example of the present invention, the present inventors biopanned a naive human single chain Fv library by a phage display method, thereby producing a human antibody B7 that binds specifically to c-Met.

As used herein, the term "biopanning" refers to a series of screening methods that select only phages, which display a peptide having the property of binding a target molecule (antibody, enzyme, cell surface receptor, etc.), from a phage library that displays peptides on the coat of phages.

Figure 6:
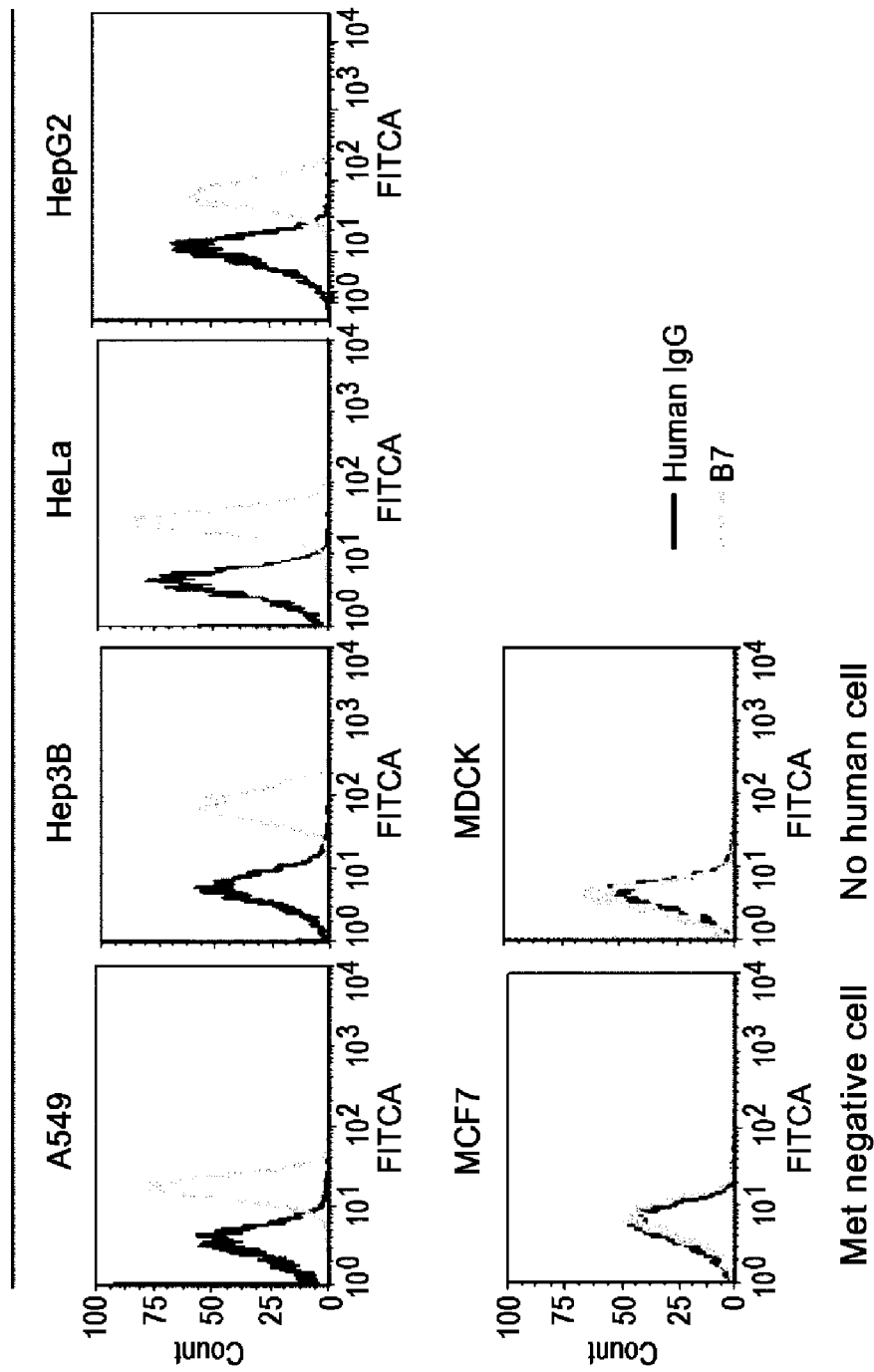
FIG. 6 is a graphic diagram showing the results of FACS analysis performed to determine whether the B7 antibody did bind to Hep3B, HeLa, A549, HepG2, MCF7 and dog kidney MDCK cells.
Figure 7:
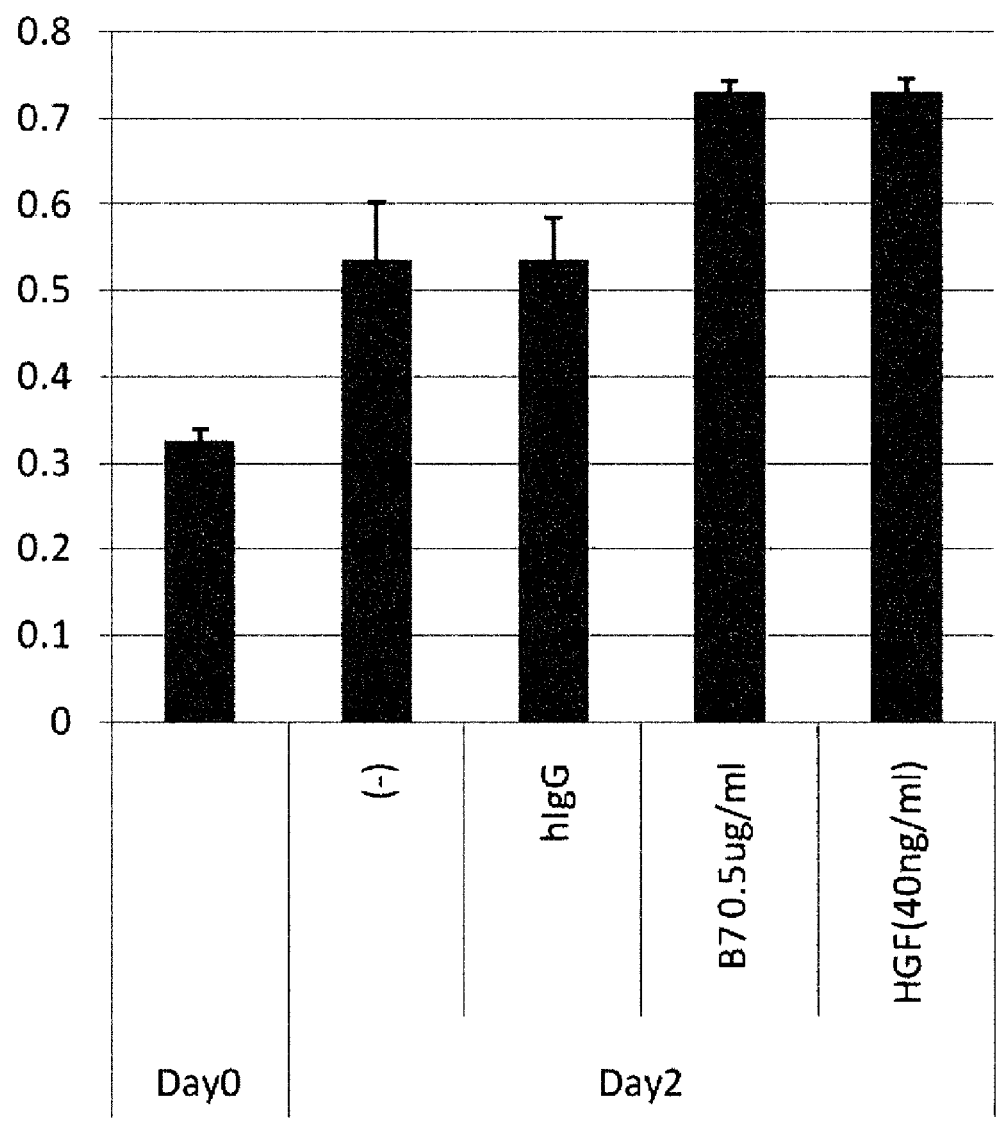
FIG. 7 is a graphic diagram showing the results of an MTT cell proliferation assay for Hep3B cells treated with HGF or B7 antibody.

In another example of the present invention, it was found by FACS that the human antibody B7 developed in the present invention did not bind to MCF7 cells known to not readily express the Met receptor therein, and dog kidney MDCK cells that express the Met receptor, but do not bind human antibodies due to the difference in species, suggesting that the antibody of the present invention is specific to c-Met (FIG. 6). Herein, the Met receptor was expressed in the dog kidney MDCK cells, but did not bind to the human antibody of the present invention binding to human c-Met antigen, due to the difference in species. An MTT cell proliferation assay showed that Hep3B cells treated with the B7 antibody in the same manner as treatment with HGF proliferated, suggesting the B7 antibody promotes cell growth in the same manner as HGF (FIG. 7). Indeed, liver cells, skin cells and brain cells were treated with HGF having wound healing activity and with the B7 antibody of the present invention, and as a result, it could be seen that the B7 antibody showed a wound healing effect, even though the effect was lower than that of HGF (FIGS. 8a to 8c).

Figure 9:
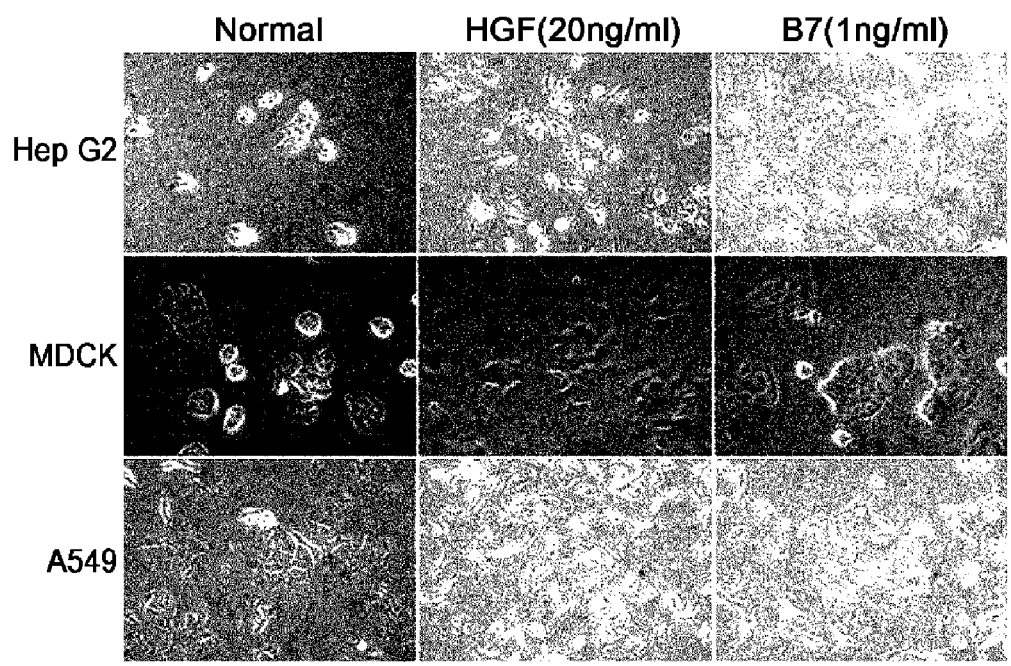
FIG. 9 is a photograph showing the scattering of HepG2, A549 and MDCK cells by HGF or the B7 antibody.
Figure 10:
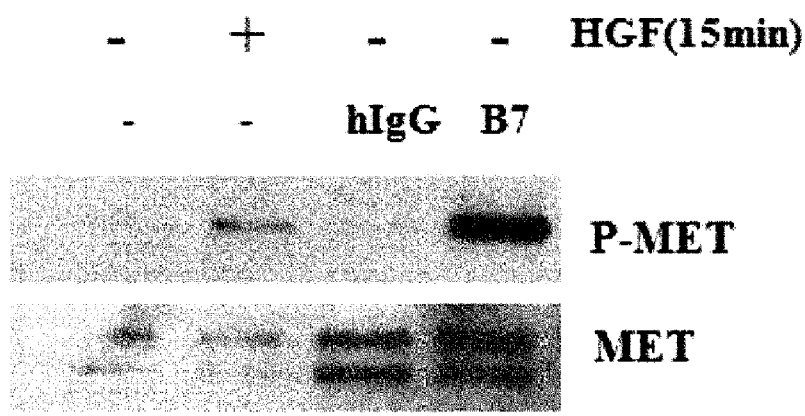
FIG. 10 is a photograph showing the B7 antibody-mediated increase in the phosphorylation of the Met receptor in human Met receptor-overexpressed Cos7 cells.
Figure 11:
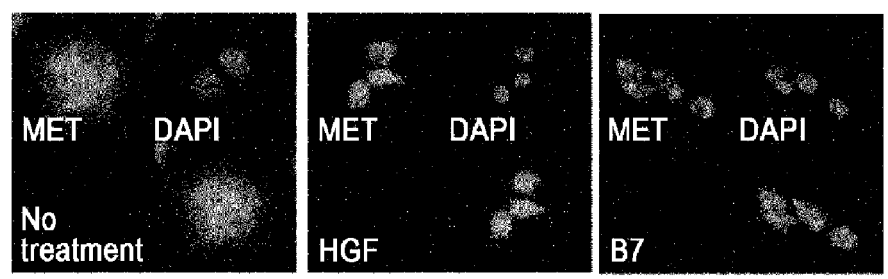
FIG. 11 is a fluorescence micrograph showing the B7 antibody-mediated increase in the intracellular internalization of the Met receptor in HeLa cells.
Figure 11:
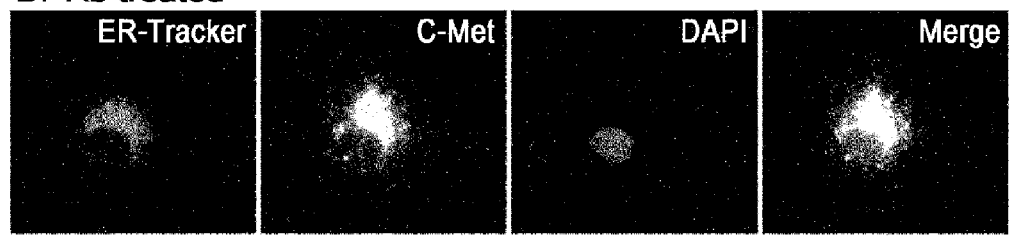

In addition, cell scattering was observed, and as a result, it was shown that the antibody of the present invention caused cell scattering that is the general property of HGF (FIG. 9). Moreover, a protein expression assay indicated that a cell group treated with the B7 antibody showed an increase in the phosphorylation of the Met receptor in the same manner as Cos7 cells treated with HGF (FIG. 10). Furthermore, an immunofluorescent staining assay indicated that endocytosis that is a typical characteristic shown by HGF was also caused by the B7 antibody (FIG. 11).

Such results support that the human antibody of the present invention can function as an HGF mimic that binds specifically to c-Met. Such results suggest that the human antibody of the present invention can function as a novel therapeutic agent for activating HGF/c-Met signaling, which overcomes the problem of plasma instability of HGF protein.

Figure 8A:
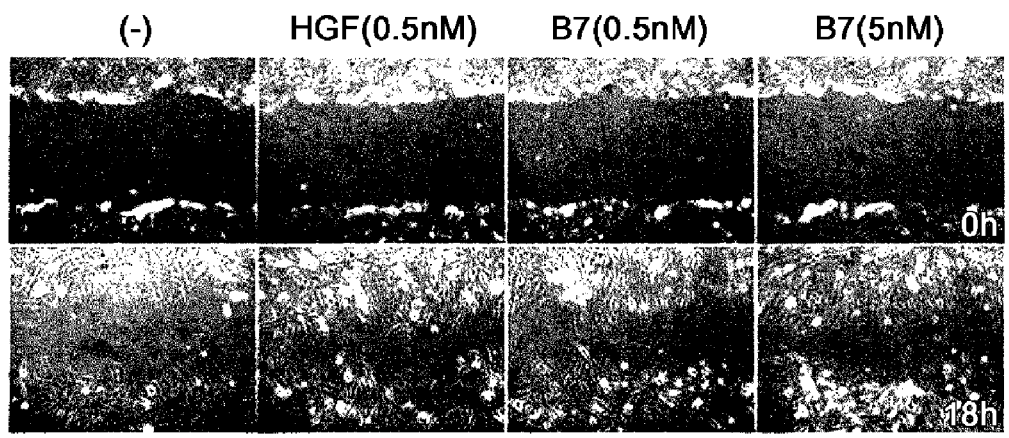
FIG. 8a is a photograph showing the effect of the B7 antibody on the repair of damaged liver cells.
Figure 8B:
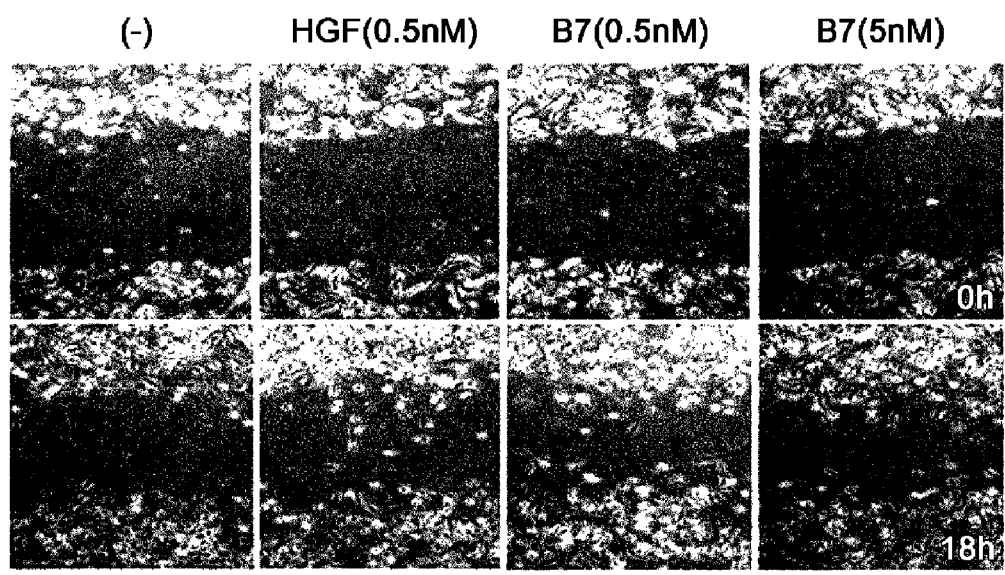
FIG. 8b is a photograph showing the effect of the B7 antibody on the repair of damaged skin cells.
Figure 8C:
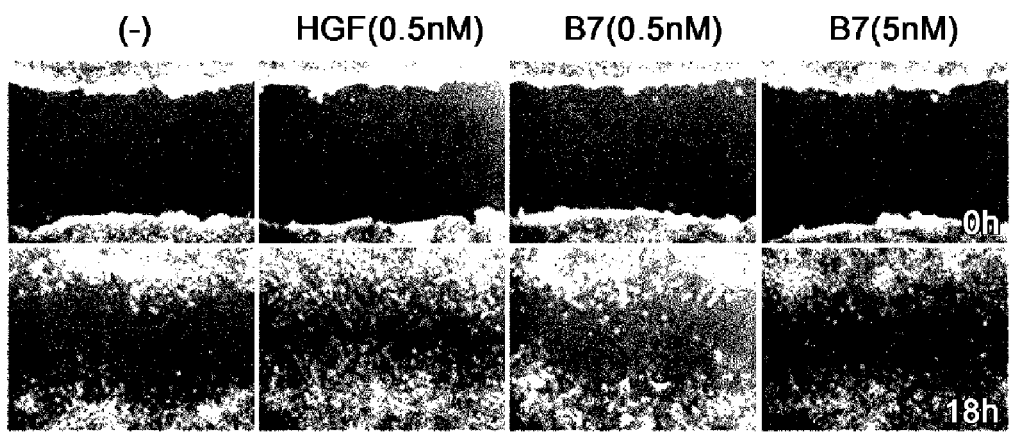
FIG. 8c is a photograph showing the effect of the B7 antibody on the repair of damaged brain cells.
Figure 13:
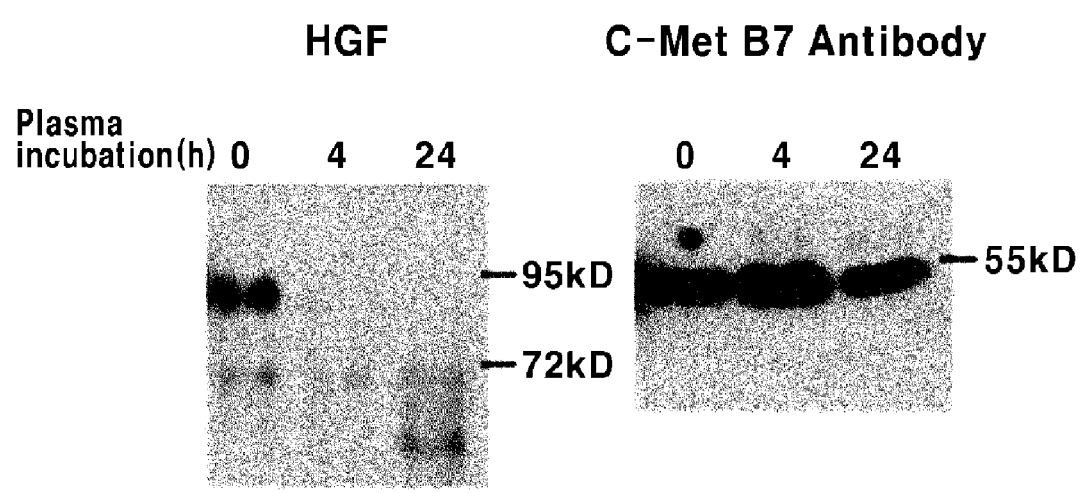
FIG. 13 is a Western blot photograph showing the difference in the stabilities of HGF and the B7 antibody in mouse plasma.

As shown in FIGS. 8a to 8c, the B7 antibody of the present invention showed a low wound healing effect compared to HGF, but showed significantly higher plasma stability compared to HGF (FIG. 13). Thus, it is expected that the B7 antibody of the present invention will actually show a higher wound healing effect compared to HGF.

In another aspect, the present invention provides a polynucleotide encoding the heavy-chain variable region and light-chain variable region of the human antibody. The polynucleotide encoding the variable regions of the antibody is inserted and expressed in an expression vector. Preferably, the polynucleotide encoding the heavy-chain variable region may be a nucleotide sequence of SEQ ID NO: 9, and the polynucleotide encoding the light-chain variable region may be a nucleotide sequence of SEQ ID NO: 10.

In still another aspect, the present invention provides an expression vector comprising the heavy-chain variable region-encoding polynucleotide and the light-chain variable region-encoding polynucleotide.

As used herein, the term "expression vector", which describes an expression vector capable of expressing a protein of interest in a suitable host cell, refers to a genetic construct that comprises essential regulatory elements to which a gene insert is operably linked in such a manner as to be expressed in a host cell.

As used herein, the term "operably linked" refers to a functional linkage between a nucleic acid expression control sequence and a nucleic acid sequence coding for a target protein in such a manner as to allow general functions. The operable linkage to a recombinant vector may be prepared using a genetic recombinant technique well known in the art, and site-specific DNA cleavage and ligation may be easily achieved using enzymes generally known in the art.

A suitable expression vector in the present invention includes expression regulatory elements, such as a promoter, an initiation codon, a stop codon, a polyadenylation signal and an enhancer, as well as signal sequences for membrane targeting or secretion. The initiation and stop codons are generally considered to be a portion of a nucleotide sequence coding for an immunogenic target protein, are necessary to be functional in a subject to which a genetic construct has been administered, and must be in frame with the coding sequence. Promoters may be generally constitutive or inducible. Non-limiting examples of promoters available in prokaryotic cells include lac, tac, T3 and T7 promoters. Non-limiting examples of promoters available in eukaryotic cells include simian virus 40 (SV40) promoter, mouse mammary tumor virus (MMTV) promoter, human immunodeficiency virus (HIV) promoter such as the HIV Long Terminal Repeat (LTR) promoter, moloney virus promoter, cytomegalovirus (CMV) promoter, epstein barr virus (EBV) promoter, rous sarcoma virus (RSV) promoter, as well as promoters from human genes such as human β-actin, human hemoglobin, human muscle creatine and human metallothionein.

An expression vector may include a selectable marker that allows selection of host cells containing the vector. Genes coding for products that confer selectable phenotypes, such as resistance to drugs, nutrient requirements, resistance to cytotoxic agents or expression of surface proteins, are used as general selectable markers. Since only cells expressing a selectable marker survive in the environment treated with a selective agent, transformed cells can be selected.

Also, a replicable expression vector may include a replication origin, a specific nucleic acid sequence that initiates replication. Also, available are viruses (e.g., vaculovirus) or phage vectors, and vectors that are able to integrate into the genome of host cells, such as retrovirus vectors. A whole antibody or antibody fragment may be produced using a vector system that simultaneously expresses a light chain and a heavy chain in a single vector, or a system that expresses a light chain and a heavy chain in two separate vectors. In the latter case, the two vectors are introduced into host cells by co-transformation or targeted transformation. In targeted transformation, cells transformed with a vector containing a light chain (or heavy chain) gene are selected, and the selected cells expressing the light chain (or heavy chain) are again transformed with a vector containing a heavy chain (light chain) gene to finally select cells expressing both light and heavy chains.

To construct an antibody in a Fab form, a vector into which genes coding for amino acids of a human light chain variable region (VL) and constant region (CL), and a human heavy chain variable region (VH) and a first constant region domain (CH1) is inserted is used.

In the polynucleotide encoding the light and heavy chains of the human antibody of the present invention, due to degeneracy of the codon or in consideration of a preferred codon in an organism where light and heavy chains of the human antibody or a fragment thereof are to be expressed, various modifications may be made in a coding region within a scope that the amino acid sequences of light and heavy chains or a fragment thereof are not changed, and various changes or modifications may be made even in portions other than the coding region within a scope that the gene expression is not affected. It will be appreciated by those skilled in the art that these modified genes are also included within the scope of the present invention. That is, one or more nucleotides may be modified by substitution, deletion, insertion, or a combination thereof as long as the polynucleotide of the present invention encodes a protein with an equivalent activity thereof, and they are also included in the present invention. The sequence of the polynucleotide may be a single or double chain, and a DNA or RNA (mRNA) molecule.

In still another aspect, the present invention provides a transformant transformed with the vector.

Host cells suitable for the vectors may be prokaryotic cells such as *Escherichia coli, Bacillus subtilis, Streptomyces, Pseudomonas, Proteus mirabilis* or *Staphylococcus*. Also, eukaryotic cells useful as host cells include lower eukaryotic cells, such as fungi (e.g., *Aspergillus* species) and yeasts (e.g., *Pichia pastoris, Saccharomyces cerevisiae, Schizosaccharomyces, Neurospora crassa*), and cells derived from higher eukaryotes, such as insect cells. Host cells may be also derived from plants and mammals. Preferred cells include, but are not limited to, COST cells (monkey kidney cells), NSO cells, SP2/0, CHO (Chinese hamster ovary) cells, W138, BHK (baby hamster kidney) cells, MDCK, myeloma cells, HuT 78 cells and 293 cells. CHO cells are preferred.

As used herein, the term "transformation into host cells" refers to any method by which nucleic acids can be introduced into organisms, cells, tissues or organs. As known in the art, the transformation may be performed by selecting suitable standard techniques according to host cells. These methods include, but are not limited to, electroporation, protoplast fusion, calcium phosphate ($CaPO_4$) precipitation, calcium chloride ($CaCl_2$) precipitation, agitation with silicon carbide fiber, agrobacterium-mediated transformation, and PEG-, dextran sulfate-, lipofectamine- and desiccation/inhibition-mediated transformation.

In still another aspect, the present invention provides a method of producing the human antibody by culturing the transformant.

Specifically, the present invention provides a method for producing the human antibody that binds specifically to c-Met, the method comprising the steps of: (i) culturing the transformant; and (ii) purifying the human antibody from the culture.

In the antibody production method, the culturing of transformant may be performed using suitable media under suitable culture conditions, which are known in the art. This culturing process may be easily adapted according to the strains selected by those skilled in the art.

The antibody obtained by culturing the transformant may be used in an unpurified form, or may be used after being purified using various general methods, which may be used separately or in combination, for example, dialysis, salt precipitation and chromatography. Among them, chromatography is most commonly used. Examples of chromatography include ion exchange chromatography, size exclusion chromatography, and affinity chromatography.

An antibody prepared by the aforementioned method has enhanced affinity to an antigen. The term "affinity" is the ability to specifically recognize and bind to a specific region of an antigen. High affinity and specificity of an antibody to an antigen are critical elements in immune responses. In the present invention, a heavy chain variable region is randomly mutated to prepare humanized heavy chain library cells, and the library cells are subjected to a colony lift assay to select mutant clones having high antigen binding capacity. The selected clones were assessed for their affinity by competitive ELISA. Other various methods, for example, surface plasmon resonance technology (SRP), may be used to measure the affinity of an antibody to an antigen.

The term "$K_D$", as used herein, refers to a dissociation constant of specific antibody-antigen interaction, and has been used to measure the affinity of an antibody to an antigen.

In still another aspect, the present invention provides a wound healing composition or a cell growth promoting composition, which comprises the human antibody as an active ingredient.

As used herein, the term "wound healing" refers to either drug treatment for repairing skin cells damaged by physical factors or protection of the damaged skin cells.

As used herein, the term "cell growth promotion" means promoting a cell regeneration process in which skin cells remaining around a skin tissue defect caused by disease or trauma rapidly divide and proliferate to migrate to the defect.

In one example of the present invention, liver, skin or brain cells were wounded by a yellow tip and then treated with the B7 antibody of the present invention. 24 hours after treatment with the antibody, it was observed that the damaged cells were repaired (FIGS. 8a to 8c). Such results support that the human antibody of the present invention can promote wound healing or cell proliferation.

By virtue of this effect, the human antibody of the present invention can be used as an active ingredient of a cosmetic composition for skin cell regeneration.

Each composition that is provided according to the present invention may comprise a pharmaceutically acceptable carrier.

As used herein, the term "pharmaceutically acceptable carrier" refers to a carrier or a diluent that does not cause significant irritation to an organism and does not abrogate the biological activity and properties of the administered compound. Examples of a pharmaceutically acceptable carrier that may be used in a composition that is formulated into a liquid solution include saline, sterile water, albumin injectable solution, dextrose solution, maltodextrin solution, glycerol, and a mixture of two or more thereof. If necessary, other conventional additives may be added, such as antioxidants, buffers and bacteriostatic agents. In addition, a diluent, a dispersant, a surfactant, a binder and a surfactant may be added to formulate the composition into injectable formulations, such as aqueous solutions, suspensions or emulsions, pills, capsules, granules or tablets.

Preferably, each composition of the present invention may be prepared as formulations for oral administration. The formulations for oral administration include, for example, troches, lozenges, aqueous or oily suspensions, powder, granules, emulsions, hard or soft capsules, syrups or elixirs. Tablet or capsule formulations may include a binder such as lactose, saccharose, sorbitol, mannitol, starch, amylopectin, cellulose or gelatin, an excipient such as dicalcium phosphate, a disintegrant such as maize starch or sweet potato starch, and a lubricant such as magnesium stearate, calcium stearate, sodium stearyl fumarate or polyethylene glycol wax. A capsule formulation may include, in addition to the above-mentioned substances, a liquid carrier such as fat oil.

In still another aspect, the present invention provides a cell regeneration composition comprising the human antibody as an active ingredient. Herein, preferred examples of the cells include, but are not limited to, liver cells, neural cells, muscle cells, skin cells and the like. More preferably, the cells may be brain cells, myocardial cells or the like.

As described above, in one example of the present invention, liver, skin or brain cells were wounded by a yellow tip and then treated with the B7 antibody of the present invention. 24 hours after treatment with the antibody, it was observed that the damaged cells were repaired (FIGS. 8a to 8c). Such results support that the human antibody of the present invention can promote regeneration of liver cells, skin cells, muscle cells, neural cells.

In yet another aspect, the present invention provides a composition for treating neurodegenerative disease, comprising the human antibody as an active ingredient. Herein, the neurodegenerative disease is preferably Parkinson's disease, ischemic disease leading to neuronal infraction, Alzheimer's disease or the like, but is not limited thereto.

In vivo and laboratory studies so far indicated that HGF/SF also acts on the nervous system, and many studies on the function of HGF/SF to protect motor neurons were reported (Novak et al., Journal of Neuroscience. 20:326-337, 2000). In addition, it was demonstrated that the HGF/MET pathway is involved in the process of neuronal infarction and that HGF is overexpressed in lesions of such neurodegenerative diseases to exhibit protective activity (Comoglio et al., Nature Review Drug Discovery. 7:504-516, 2008).

Therefore, HGF/SF can be used as agents for preventing the death of neurons in the central nervous system and for treating neurodegenerative diseases, including Parkinson's disease, ischemic disease leading to neuronal infraction, Alzheimer's disease or the like. Such results support that the c-Met-specific human antibody of the present invention, which induces HGF/SF signaling, can be used as an active ingredient of a composition for treating neurodegenerative diseases.

In still another aspect, the present invention provides a composition for treating ulcerative damage to an organ, comprising the human antibody as an active ingredient. Herein, preferred examples of the organ include, but are not limited to, heart, kidney, liver and lung.

The present inventors previously reported that the deregulation of HGF/SF-Met signaling does not influence the usual function of hepatocytes, but adversely affects the regeneration of damaged hepatocytes. Since then, the present inventors confirmed that, when the skin in addition to the liver is damaged, HGF/SF and c-Met are secreted. In other words, large amounts of HGF/SF and c-Met are secreted from hyperproliferative skin tissue to promote the proliferation of skin cells. However, it was reported that c-Met is found in the skin and hair follicles, whereas HGF/SF is usually expressed only in hair follicles and is found in damaged skin. Thus, HGF/SF remains in an inactivated state until the skin is damaged, and it is activated around wounds after the skin is damaged (Journal of Cell Biology 177(1):151-162, 2007). Accordingly, it is known that HGF/c-Met directly regulate skin regeneration and repair (Nakamura et al., Nature. 342:440-443, 1993; Huh et al., Proc Natl Acad Sci USA. 101:4477-4482, 2004).

In addition, it was suggested that HGF/SF plays an important role in defensive physiological mechanisms following general organ damage such as myocardium damage (Nakamura et al., J Clin Invest. 106:1511-1519, 2000). Thus, HGF/SF can be used as an agent for treating damage to heart, kidney, liver, lung or the like, which is caused by various factors. Such results support that the c-Met-specific human antibody of the present invention, which induces HGF/SF signaling, can be used as an active ingredient of a composition for treating ulcerative damage to an organ.

In still another aspect, the present invention provides a method for wound healing, treatment of neurodegenerative disease or treatment of ulcerative damage to an organ, the method comprising administering a pharmaceutically effective amount of the human antibody to a subject.

As used herein, the term "treatment" refers to all actions that enhance wound healing, skin regeneration, treatment of neurodegenerative disease or treatment of ulcerative damage to an organ, by administration of the composition.

The treatment method of the present invention comprises administering a pharmaceutically effective amount of the antibody. It will be obvious to those skilled in the art that the suitable daily dose of the antibody can be determined by the physician within the range of reliable medical decisions. It may be administered once or several times. As for any specific patients, the therapeutically effective amount is preferably determined based on various factors, including the diseases to be treated and severity thereof, the activity of the used specific compound, the used specific composition, the age, body weight, general health status, gender and food of patient, the administration time and route and excretory rate of the used specific compound, the drug administered in combination or simultaneously with the specific compound, and similar factors well known in the art of medicine.

The subject to which the composition of the present invention is to be administered include, without limitation, mammals including humans, and examples thereof include cow, pig, horse, rabbit, rat and human.

As used herein, the term "administration" means introducing the pharmaceutical composition of the present invention by any suitable method. The composition of the present invention may be administered through any oral or parenteral route through which the composition can reach the target tissue.

In still another aspect, the present invention provides a drug conjugate comprising a drug linked to the human antibody.

As used herein, the term "drug" refers to a compound that can bind to the c-Met-specific human antibody of the present invention, can be separated from the human antibody under an acidic condition and exhibits a therapeutic effect on a target cell. Examples of the drug include, but are not limited to, doxorubicin, nitrogen mustard, chlorambucil, melphalan, cyclophosphamide, thiotepa, busulfan, dacarbazine (DTIC), procarbazine, BCNU, CCNU, methyl-CCNU, methotrexate (MTX), 6-mercaptofuran (6-MP), 6-thioguanine, 5-fluorouracil, cytarabine, adriamycin, daunorubicin, bleomycin, mitomycin-C, actinomycin-D, vincristine, vinblastine, VP-16-213, VM-26, tamoxifen, cisplatin, L-asparaginase, o,p-DDD, IFN, IL-2, thymosin $\alpha$-1, bleomycin, mitomycin C, cyclophosphamide, aclarubicin, aspirin, ibuprofen, naproxen, acetaminophen, and the like.

The drug conjugate comprising a drug linked to the human antibody of the present invention can be introduced into a cell by receptor-mediated endocytosis, and the drug can be separated from the antibody under an acidic environment in the cell to exhibit its function. Thus, the drug conjugate can be used as an antibody for target cell treatment.

In yet another aspect, the human antibody of the present invention can be used for the preparation of therapeutic compositions showing various effects.

Examples of therapeutic compositions that can be prepared using the human antibody include, but are not limited to, wound healing compositions, cell regeneration compositions, compositions for treating neurodegenerative diseases, compositions for treating ulcerative damage to organs, etc.

MODE FOR INVENTION

Hereinafter, the present invention will be described in further detail with reference to examples. It is to be understood, however, that these examples are for illustrative purposes only and are not intended to limit the scope of the present invention.

Example 1

Preparation of Antibody

To prepare B7 antibody, a known phage display method was used. Specifically, the variable region of the B7 phage appearing to bind to the Met receptor was cloned into a pNATAB vector to obtain heavy-chain DNA and light-chain DNA. The obtained DNAs and a PEI reagent were mixed with a serum-free DMEM medium. Then, 293E cells were treated with the mixture so that the B7 antibody was secreted into the medium. Next, the B7 antibody was purified from the medium.

Example 1-1

Preparation of Library Phage $2.7 \times 10^{10}$ human scFv library cells having diversity were cultured at 37° C. for 2-3 hours in a medium (3 L) containing 2×YT CM [tryptone (CONDA, 1612.00) 17 g, yeast extract (CONDA, 1702.00) 10 g, NaCl (Sigma, S7653-5 kg) 5 g, chloramphenicol (Sigma, C0857) 34 µg/ml], 2% glucose (Sigma, G5400) and 5 mM $MgCl_2$ (Sigma, M2393) (OD600=0.5-0.7). Then, the cells were transfected with a helper phage and cultured in 2×YTCMK [2×YT CM, kanamycin (Sigma, K1876) 70 µg/ml, 1 mM IPTG (ELPIS-BIO, IPTG025)] medium at 30° C. for 16 hours. The cultured cells were centrifuged (4500 rpm, 15 min, 4° C.), and then 4% PEG (Fluka, 81253) 6000 and 3% NaCl (Sigma, 57653) were added to and dissolved in the supernatant and allowed to react on ice for 1 hour. The reaction solution was centrifuged (8000 rpm, 20 min, 4° C.), and the pellets were suspended in PBS, followed by centrifugation (12000 rpm, 10 min, 4° C.), thereby preparing a library phage.

Example 1-2

Panning Process

30 µg of purified c-Met (extracellular domain)-Fc was added to and dissolved in 4 ml of coating buffer [$Na_2CO_3$ (Sigma, S7795) 1.59 g, $NaHCO_3$ (Sigma, 58875) 2.93 g, $NaN_3$ (Sigma, 52002) 0.2 g], and the solution was placed in an immunosorb tube (Nunc 470319) which was then maintained in a rotator at 4° C. for 16 hours to coat c-Met on the wall of the tube. Then, the coated c-Met was blocked using 4% skim milk (BD, 232100) in PBS.

To the coated immunosorb tube, 2 ml of the library phage prepared in Example 1-1 was added and allowed to react at room temperature for 2 hours, and then the tube was washed five times with PBST (0.05%) and twice with PBS. After washing, specifically bound scFv-phages were eluted with 100 mM TEA (Sigma T-0886), and the eluted phages were transfected into E. coli (XL1-Blue, Stratagene, 200249) and amplified. The amplified phages were washed five times in first panning, 13 times in second panning and 23 times in third panning (Table 1).

TABLE 1

Comparison of antibody titer between panning stages

| Number of pannings | Number of phages introduced | Number of phages bound | Number of washings | Amount of antigen |
|---|---|---|---|---|
| 1 | $4.0 \times 10^{13}$ | $4.5 \times 10^7 / 2.7 \times 10^7 / 3.9 \times 10^7$ | 5 | 30 µg |
| 2 | $6.0 \times 10^{13}$ | $7.5 \times 10^6$ | 13 | 30 µg |
| 3 | $6.0 \times 10^{13}$ | $6.0 \times 10^9$ | 23 | 30 µg |

As can be seen in Table 1 above, as the number of pannings increased, the antibody titer increased.

Example 1-3

Phage Antibody Screening by Phage ELISA

The cell stock, panned 1-3 times and thawed, was added to 5 ml of primary medium (2×YTCM, 2% Glucose, 5 mM MgCl2) to OD600=0.1, and then incubated at 37° C. for 2-3 hours (OD600=0.5-0.7). Then, the cells were transfected with M1 helper phage and cultured in secondary medium (2×YTCMK, 5 mM MgCl2, 1 mM IPTG) at 30° C. for 16 hours. The incubated cells were centrifuged (4500 rpm, 15 min, 4° C.), and the supernatant (panned poly scFv-phage) was transferred into a fresh tube. Each well of a 96-well immunoplate (NUNC 439454) was coated with 100 mg of antigen by treatment with coating buffer at 4° C. for about 16 hours, and then each well was blocked skim milk (4%) in PBS. Each well was washed with 0.2 ml of PBS-tween20 (0.05%), and 100 µl of each of 0, 5, 25, 125, 625 and 3125-fold dilutions of the panned poly scFV-phage was added to each well and allowed to react at room temperature for 2 hours. Next, each well was washed 4 times with 0.2 ml of PBS-tween 20 (0.05%), and then allowed to react with a 1:2000 dilution of secondary antibody anti-M13-HRP (Amersham 27-9421-01) at room temperature for 1 hour.

After washing with 0.2 ml of PBS-tween 20 (0.05%), 100 µl of a substrate solution of OPD tablet (Sigma 8787-TAB) in PC buffer [$C_6H_8O_7 \cdot H_2O$ (Sigma, C0706) 5.1 g, $Na_2HPO_4$ (Sigma, 57907) 7.3 g] was added to each well to develop color. After 10 minutes, the absorbance at 490 nm was measured (FIG. 1). FIG. 1 shows the results of ELISA for the c-Met polyclonal antibody. As can be seen in FIG. 1, the ability to bind to the antibody started to increase from the second polyclonal scFv-phage pool and reached a saturated state in the third pool.

Example 1-4

Selection of Monoclonal Antibody

A colony obtained from the polyclonal phage antibody group having high binding ability was cultured in a 96-well plate (Bioneer 90030) containing 1 ml of medium (2×YTCM, 2% glucose, 5 mM $MgCl_2$) at 37° C. for 16 hours. When the OD600 value reached 0.1, 100-200 µl of the cell culture was diluted in 1 ml of primary medium, and then incubated in a 96-deep well plate at 37° C. for 2-3 hours until the OD600 value reached 0.5-0.7. Next, the cells were transfected with M1 helper phage such that the MOI value was 1:20, after which the cells were incubated in secondary medium at 30° C. for 16 hours. The incubated cells were centrifuged (4500 rpm, 15 min, 4° C.), and the supernatant was added to 4% PEG 6000 and 3% NaCl and allowed to react on ice for 1 hour. Next, the reaction solution was centrifuged (8000 rpm, 20 min, 4° C.), and then the pellets were added to and dissolved in PBS, followed by centrifugation (12000 rpm, 10 min, 4° C.). The supernatant was transferred into a fresh tube and stored at 4° C. Next, each well of a 96-well plate was coated with 100 ng of antigen at 4° C. for 16 hours, and then each well was blocked with skim milk (4%) in PBS. Each well was washed with 0.2 ml of PBS-tween 20 (0.05%), and then 100 µl of the monoclonal phage (each 100 scFv-phage) obtained as described above was added to each well and allowed to react at room temperature for 2 hours. Next, each well was washed four times with 0.2 ml of PBS-tween 20 (0.05%), and then allowed to react with a ¹/₂₀₀₀ dilution of anti-M13-HRP secondary antibody for 1 hour. Then, each well was washed with 0.2 ml of PBS-tween 20 (0.05%), after which color development was performed and the absorbance at 490 nm was measured (Tables 2 and 3).

TABLE 2

Mono-phage ELISA of 2$^{nd}$ monoclones for c-met-Fc

|  | A | B | C | D | E | F | G | H |
|---|---|---|---|---|---|---|---|---|
| C-met(100 ng/well) | 0.156 | 0.089 | 0.092 | 1.414 | 1.825 | 0.427 | 1.189 | 2.805 |
|  | 0.812 | 1.359 | 1.770 | 0.112 | 0.785 | 1.721 | 3.386 | 2.789 |
|  | 0.057 | 0.067 | 0.070 | 0.127 | 0.147 | 0.058 | 0.064 | 2.666 |
|  | 1.627 | 0.957 | 0.045 | 2.470 | 0.081 | 2.621 | 0.201 | 1.182 |
|  | 1.654 | 0.291 | 0.680 | 0.754 | 0.841 | 2.682 | 0.689 | 0.086 |
|  | 0.807 | 0.087 | 1.330 | 1.297 | 0.052 | 1.206 | 0.594 | 2.673 |
| anti-myc(100 ng/well) | 0.869 | 0.998 | 1.359 | 2.508 | 1.522 | 2.491 | 2.581 | 2.548 |
|  | 2.577 | 2.625 | 2.624 | 2.485 | 2.705 | 2.687 | 2.628 | 2.782 |
|  | 0.052 | 0.827 | 2.136 | 2.259 | 2.351 | 0.688 | 0.393 | 2.626 |
|  | 2.686 | 2.565 | 0.062 | 2.570 | 2.525 | 2.567 | 2.626 | 2.609 |
|  | 2.583 | 2.551 | 2.614 | 2.526 | 2.605 | 2.609 | 2.523 | 2.135 |
|  | 2.613 | 1.232 | 2.584 | 2.577 | 0.057 | 2.668 | 2.695 | 2.744 |
| Fc | 0.290 | 0.201 | 0.118 | 0.194 | 0.722 | 0.178 | 0.504 | 2.537 |
|  | 0.224 | 0.351 | 0.519 | 0.206 | 1.020 | 0.541 | 2.577 | 1.661 |
|  | 0.076 | 0.084 | 0.150 | 0.446 | 0.113 | 0.090 | 0.221 | 2.370 |
|  | 0.591 | 0.204 | 0.079 | 2.024 | 0.230 | 2.196 | 0.192 | 0.218 |
|  | 0.119 | 0.160 | 0.133 | 0.123 | 0.122 | 2.150 | 0.116 | 0.227 |
|  | 1.176 | 0.118 | 0.106 | 0.119 | 0.126 | 0.453 | 0.158 | 2.490 |

TABLE 3

Mono-phage ELISA of 3$^{rd}$ monoclones for c-met-Fc

|  | A | B | C | D | E | F | G | H |
|---|---|---|---|---|---|---|---|---|
| C-met(100 ng/well) | 2.899 | 2.890 | 2.835 | 2.861 | 0.488 | 0.066 | 0.066 | 2.923 |
|  | 2.807 | 2.742 | 0.063 | 0.052 | 0.060 | 0.059 | 2.826 | 2.821 |
|  | 2.807 | 2.755 | 2.753 | 2.588 | 2.797 | 2.761 | 0.075 | 2.776 |
|  | 0.082 | 0.062 | 2.747 | 2.677 | 1.998 | 2.833 | 2.862 | 0.291 |
|  | 2.752 | 2.729 | 2.681 | 0.061 | 2.678 | 2.719 | 2.656 | 2.545 |
|  | 2.670 | 2.618 | 2.714 | 1.026 | 2.755 | 2.754 | 2.515 | 2.743 |
| anti-myc(100 ng/well) | 2.621 | 2.564 | 2.543 | 2.607 | 2.521 | 0.125 | 0.059 | 2.535 |
|  | 2.605 | 2.624 | 0.053 | 0.054 | 0.334 | 0.054 | 2.645 | 2.665 |
|  | 2 704 | 2.683 | 2.689 | 1.846 | 2.640 | 2.564 | 0.054 | 2.593 |
|  | 0.065 | 0.061 | 2.692 | 2.062 | 0.414 | 2.662 | 2.641 | 0.091 |
|  | 2.736 | 2.590 | 2.666 | 0.062 | 2.636 | 2.620 | 2.582 | 1.360 |
|  | 2.701 | 1.917 | 2.222 | 2.624 | 2.544 | 2.585 | 1.784 | 1.936 |
| Fc | 2.381 | 0.148 | 2.008 | 2.474 | 0.122 | 0.112 | 0.100 | 2.533 |
|  | 1.920 | 2.452 | 0.122 | 0.124 | 0.155 | 0.129 | 2.494 | 1.315 |
|  | 2.384 | 2.505 | 2.518 | 1.360 | 2.485 | 0.154 | 0.233 | 2.519 |
|  | 0.148 | 0.083 | 2.490 | 2.387 | 0.100 | 2.184 | 2.501 | 0.278 |
|  | 2.544 | 0.198 | 2.563 | 0.142 | 2.467 | 2.554 | 2.557 | 2.124 |
|  | 2.463 | 1.801 | 2.485 | 0.190 | 0.236 | 2.546 | 1.194 | 2.596 |

As can be seen in Tables 2 and 3 above, 23 mono phage clones having a binding ability of 1 or higher to the antigen could be selected.

Example 1-5

Examination of Monoclonal Phages by Fingerprinting

1 µl of the primarily selected 16 monoclones for c-Met-Fc, 0.2 µl of Taq.DNA polymerase (Gendocs, 5 U/µl), 0.2 µl of each of 50 p/µl forward primer (pYG100-F) and reverse primer (pYG100-R), 0.6 µl of 10× buffer, 0.6 µl of 10 mM dNTP mix and 24.8 µl of distilled water were mixed with each other and subjected to colony PCR (iCycler iQ, BIO-RAD) under the following conditions: 1 cycle of 95° C. for 5 min, 34 cycles of 95° C. at 20 sec, 48° C. at 40 sec and 72° C. at 1 min, and 1 cycle of 72° C. at 5 min.

pYG100-F:
(SEQ ID NO: 11)
5'-cagctatgaccatgattacg-3' pYG100-R:
(SEQ ID NO: 12)
5'-cttattagcgtttgccatct-3'

The colony PCR product was analyzed on 1% agarose gel (Seakem LE, CAMERES 50004), and 0.2 µl of BstNI (Roche11288075001, 10 U/µl) was added thereto and allowed to react at 37° C. for 2-3 hours. The reaction was performed using 3 µl of 10× buffer, 10 µl of the PCR product, 0.2 µl of BstNI (10 U/µl) and 16.8 µl of distilled water.

Figure 2A:
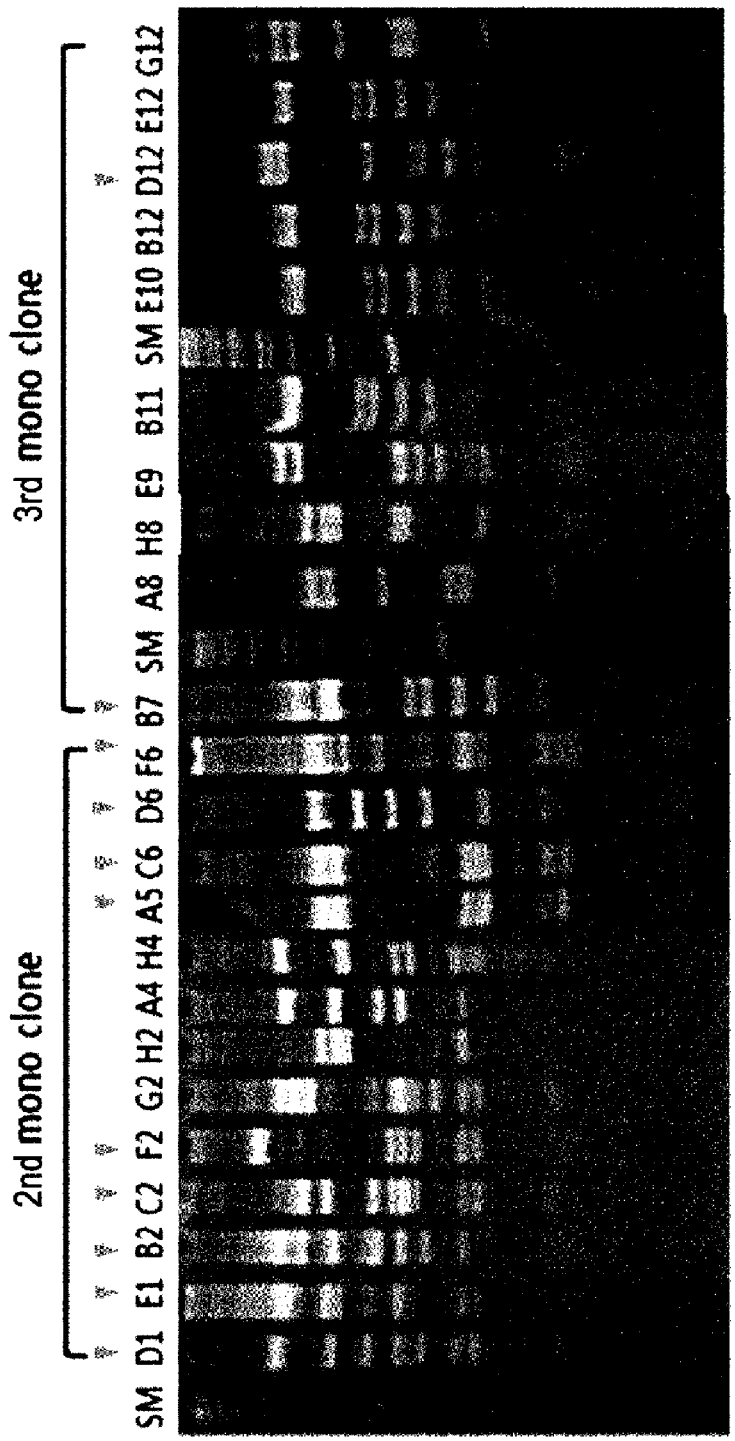
FIGS. 2a and 2b are electrophoresis photographs showing the results of fingerprinting for c-Met monoclonal phages.
Figure 2B:
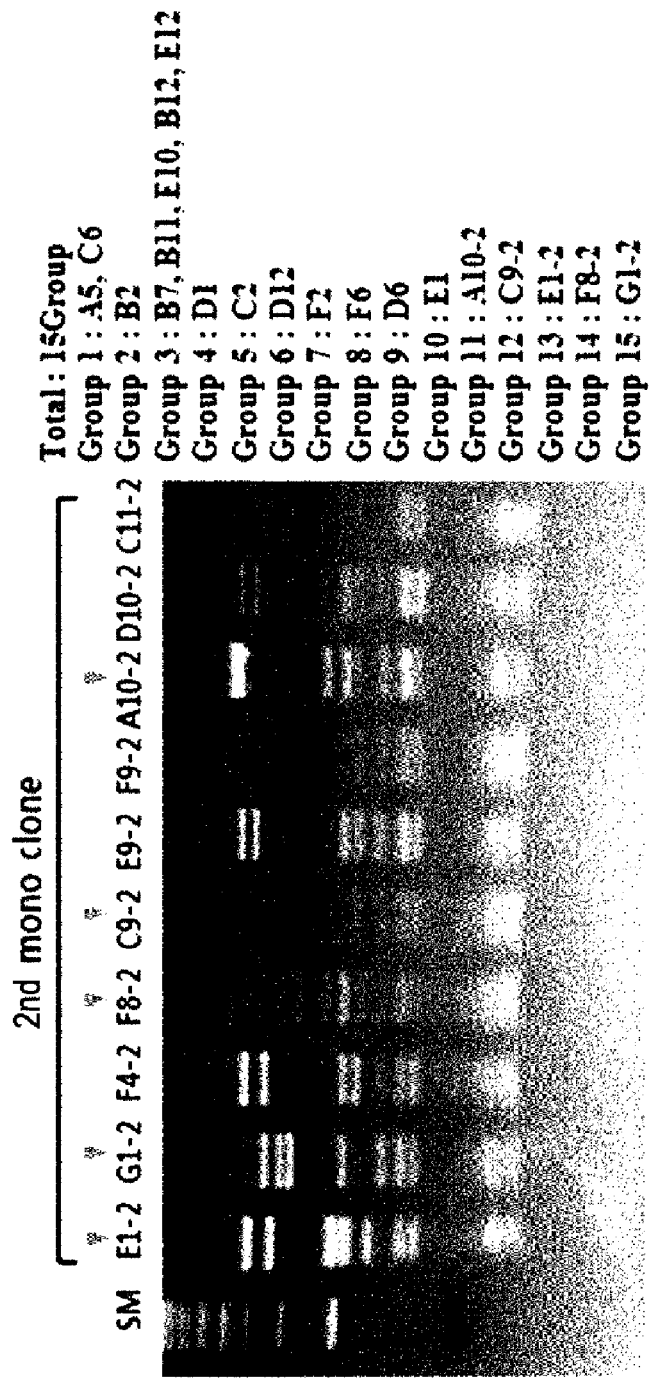

The diversity of the digested products was analyzed on DNA polyacrylamide gel (30% acrylamide (Bio-RAD, 161-0156) 2.66 ml, 10×TBE 1 ml, dH$_2$O 6.27 mil, 10% APS (sigma, A3678) 70 µl, TEMED (Bio-RAD, 161-0801) 7 µl) by monoclonal phage antibody fragments digested by BstNI (FIGS. 2a and 2b). FIGS. 2a and 2b are electrophoresis photographs showing the results of fingerprinting for the c-Met monoclonal phages. As can be seen in FIGS. 2a and 2b, diversity was observed for the monoclonal phage antibodies digested by BstNI, and 15 kinds of different antibodies were screened.

Example 1-6

Examination of Monoclonal Phages by Sequencing 15 kinds of monoclonal phage clones for c-Met-Fc were inoculated in 5 ml of medium (2×YTCM, 2% glucose, 5 mM MgCl$_2$) and incubated at 37° C. for 16 hours. From the incubated monoclonal clones, DNAs were collected using a DNA purification kit (Nuclogen 5112), and the sequences thereof were analyzed (Table 4).

TABLE 4

Characteristics of C-met-Fc specific and selected scFv clones

| Name | VH (similarity) | VL (similarity) | VH (SEQ ID NO) | Vk (SEQ ID NO) | c-Met | Anti-myc | Fc | Group |
|---|---|---|---|---|---|---|---|---|
| A5 | VH3-53 (93.0) | V2-13 (93.8) | 17 | 32 | 1.654 | 2.583 | 0.119 | 1 |
| B2 | VH3-53 (89.0) | V1-3 (96.3) | 18 | 33 | 1.359 | 2.625 | 0.351 | 2 |
| B7 | VH3-34 (89.7) | V1-4 (89.7) | 19 | 34 | 2.89 | 2.564 | 0.148 | 3 |
| D1 | VH3-53 (96.2) | V1-4 (97.3) | 20 | 35 | 1.414 | 2.508 | 0.194 | 4 |
| C2 | VH3-23 (91.9) | V1-13 (94.9) | 21 | 36 | 1.77 | 2.624 | 0.519 | 5 |
| D12 | VH3-49 (98.3) | A27 (97.5) | 22 | 37 | 1.026 | 2.624 | 0.19 | 6 |
| F2 | VH3-23 (88.8) | O12 (89.8) | 23 | 38 | 1.721 | 2.687 | 0.541 | 7 |
| F6 | VH3-23 (95.9) | O12 (95.2) | 24 | 39 | 1.206 | 2.668 | 0.453 | 8 |
| D6 | VH3-23 (95.2) | L11 (95.1) | 25 | 40 | 1.297 | 2.577 | 0.119 | 9 |
| E1 | VH3-23 (93.9) | L5 (94.0) | 26 | 41 | 1.825 | 1.522 | 0.722 | 10 |
| A10-2 | VH3-15 (92.7) | L8 (93.0) | 27 | 42 | 0.919 | 1.902 | 0.410 | 11 |
| C9-2 | VH3-23 (91.4) | V1-13 (90.8) | 28 | 43 | 0.962 | 1.186 | 0.134 | 12 |
| E1-2 | VH3-23 (91.4) | V1-13 (92.8) | 29 | 44 | 1.106 | 1.736 | 0.317 | 13 |
| F8-2 | VH3-2 (87.7) | VH1-8 (92.2) | 30 | 45 | 1.157 | 1.107 | 0.314 | 14 |
| G1-2 | VH3-15 (98.7) | L5 (97.2) | 31 | 46 | 0.814 | 1.700 | 0.282 | 15 |

As can be seen in Table 4 above, the VH, VL and CDR regions of the selected antibodies were confirmed, the amino acid sequences of CDR3 in the heavy chain and light chain of the antibodies were analyzed and had different sequences.

Example 1-7

Analysis of Whole IgG Conversion

In order to convert monoclonal phage antibodies against c-Met from phage to whole IgG vector, 1 μl of heavy chain monoclonal DNA, 10 pmole/μl of each of the following heavy-chain forward primer (NATVH4-2) and heavy chain reverse primer (NATJH-ALL Nhe I), 5 μl of 10× buffer, 1 μl of 10 mM dNTP mix, 0.5 μl of pfu DNA polymerase (Solgent, 2.5 U/μl), and distilled water (iCycler iQ, BIO-RAD) were mixed to perform a colony PCR (iCycler iQ, BIO-RAD). The PCR was performed under the following conditions: 1 cycle of 95° C. at 2 min, 30 cycles of 95 for 20 sec, 55° C. for 40 sec and 72° C. 1 min, and 1 cycle of 72 for 5 min.

NATVH4-2:
(SEQ ID NO: 13)
5'-TTGGTGGCCACAGCGGCCGATGTCCACTCGCAGGTGCAGCTACAGC
AGTG-3'

NATJH-ALL Nhe I:
(SEQ ID NO: 14)
5'-GAGGAGGCTAGCTGAGGAGACGGTGA-3'

In addition, the light chain was also subjected to colony PCR in the same manner as above using the following light-chain forward primer (NATVL4) and reverse primer (NATJL2-R).

NATVL4:
(SEQ ID NO: 15)
5'-TTGGTGGCCACAGCGGCCGATGTCCACTCGCAGTCTGCCCTGACTC
AGCC-3'

NATJL2-R:
(SEQ ID NO: 16)
5'-GAGGAGAGATCTTAGGACGGTCAGCTTGGTCCC-3'

Figure 3A:
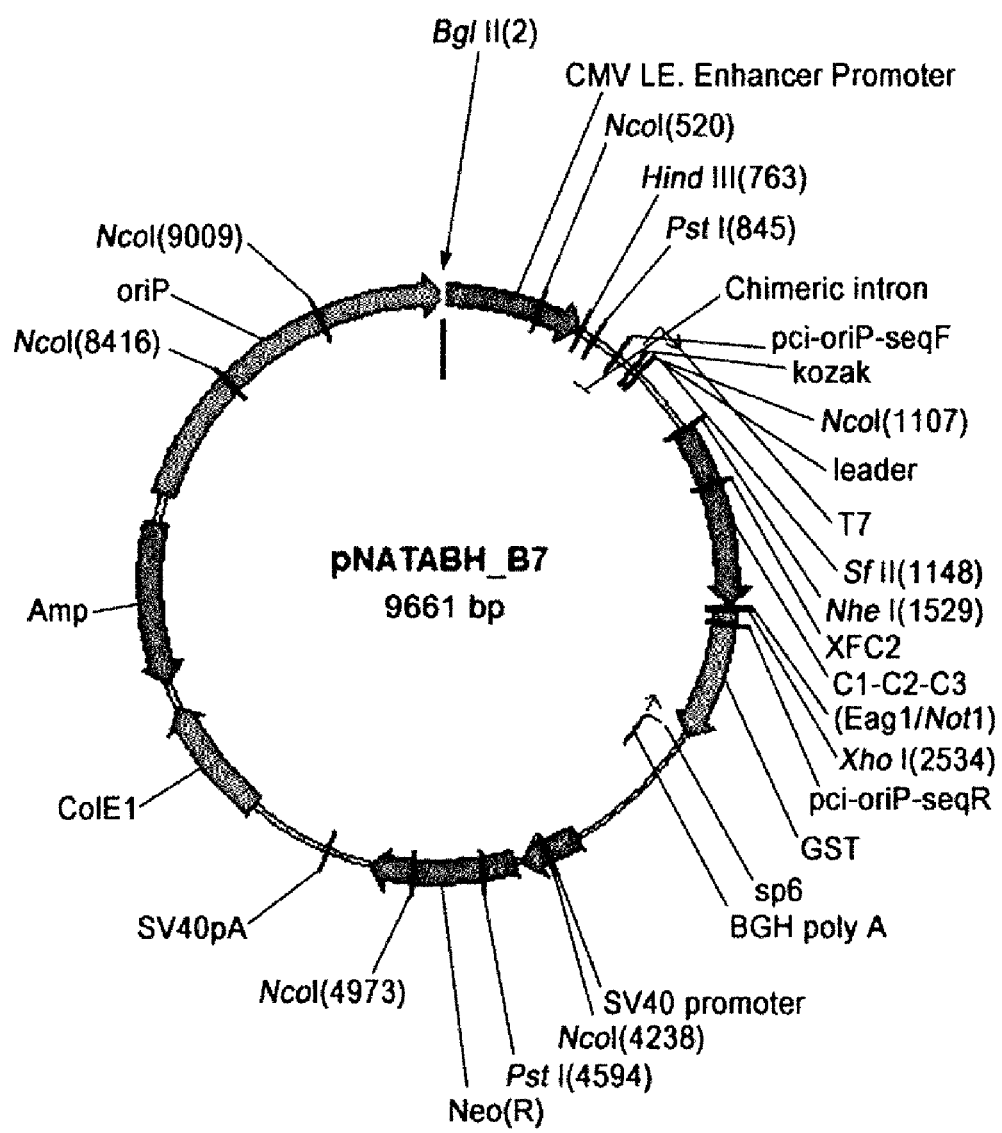
FIG. 3a is a vector map showing the heavy-chain expression vector pNATABH_B7.

The heavy chain gene obtained through PCR was purified with a DNA-gel extraction kit (Qiagen). 1 μl of pNATABH vector (10 ng), 15 μl of heavy chain (100-200 ng), 2 μl of 10× buffer, 1 μl of ligase (1 U/μl), and distilled water were mixed with the gene and the mixture was allowed to stand at room temperature for 1-2 hours for linkage to the vector, thereby constructing the heavy-chain expression vector pNATABH_B7 (FIG. 3a). FIG. 3a is a vector map showing the heavy-chain expression vector pNATABH_B7 (FIG. 3a). The vector was allowed to stand on ice for 30 minutes along with a cell for transformation (XL1-blue), followed by heat shock at 42° C. for 90 sec for transfection. It was again left to stand on ice for 5 minutes and 1 ml of LB medium was injected, followed by incubation at 37° C. for 1 hour. The mixture was inoculated in LB Amp liquid medium, followed by incubation at 37° C. for 16 hours. Single colony was inoculated into 5 Ml of LB Amp liquid medium, followed by incubation at 37° C. for 16 hours. A DNA-prep kit (Nuclogen) was used to extract DNA from the medium.

Figure 3B:
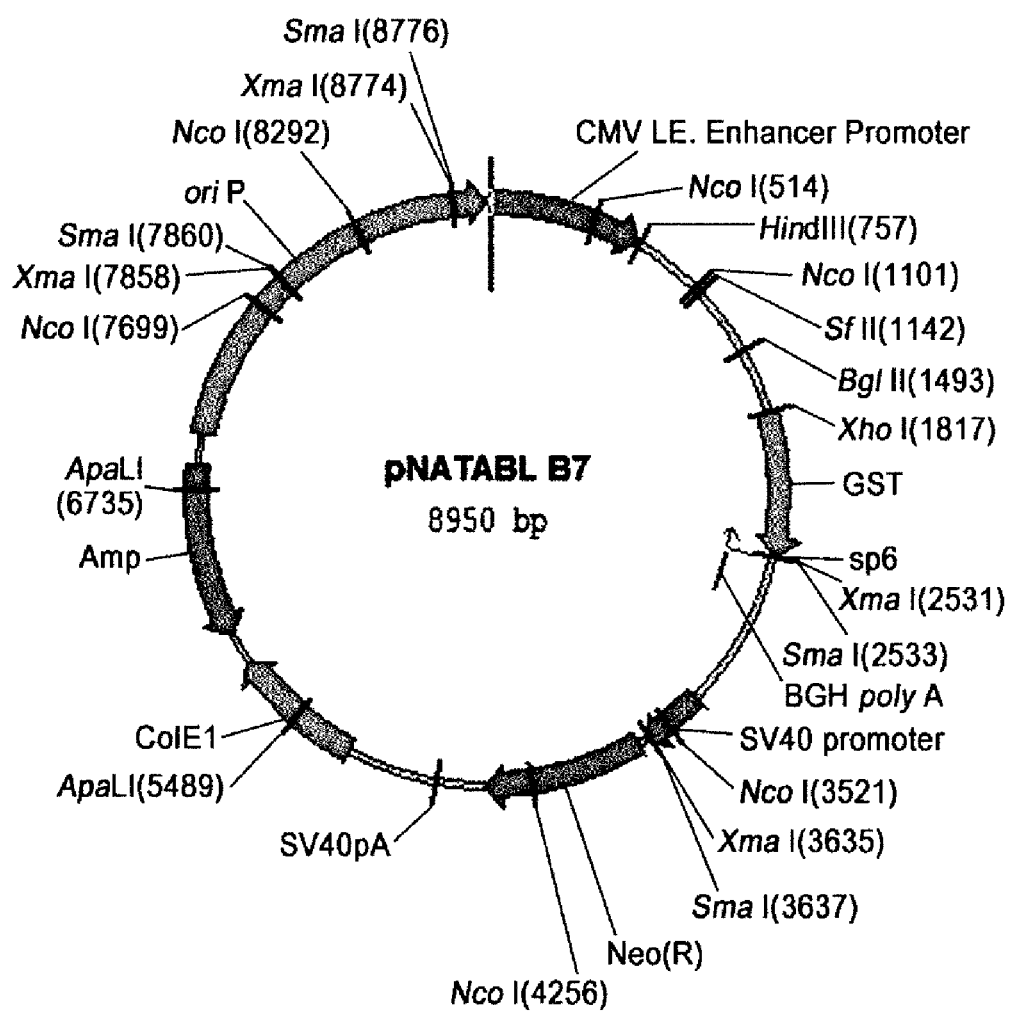
FIG. 3b is a vector map showing the light-chain expression vector pNATABL_B7.

Meanwhile, the light-chain expression vector pNAT-ABL_B7 (FIG. 3b) was constructed in the same manner as above using the pNATABL vector and was used to extract light-chain DNA. FIG. 3b is a vector map showing the light-chain expression vector pNATABL_B7.

Sequencing of the obtained DNA was performed by using a CMV-proF primer (SEQ ID NO 9: 5'-AAATGGGCGG-TAGGCGTG-3'). As a result, it was confirmed that the sequences of heavy and light chains of the 15 clone phages against c-Met-Fc converted into whole IgG were identical to those of the phage antibodies.

Example 1-8

Antibody Expression and Purification

Figure 4:
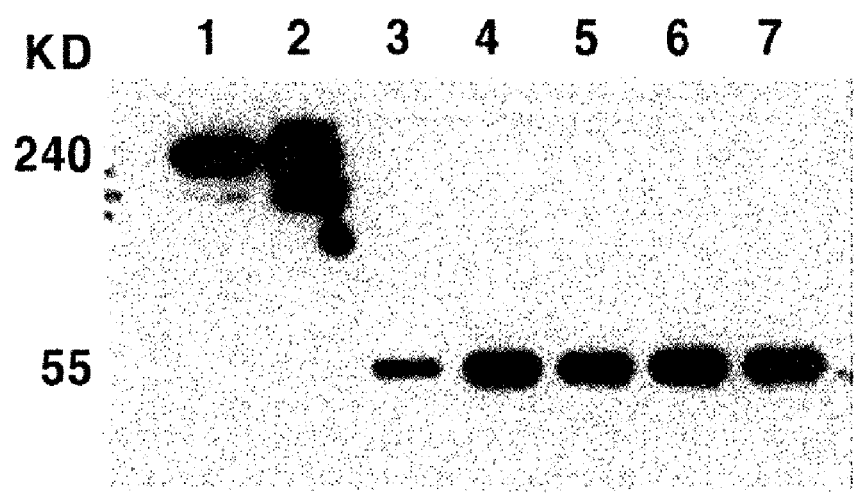
FIG. 4 is a photograph showing the results of Western blot analysis performed to determine whether an antibody was expressed.

PEI reagent and the heavy chain and light chain DNAs obtained by cloning the variable region of B7 phage into the pNATAB vector were mixed with serum-free DMEM medium, and 293E cells were treated with the mixture and cultured. When the 293E cells reached a confluence of about 70% in a 100 mm plate, 6 μg of each of the heavy-chain and light-chain DNAs and 20 μg of PEI (#23966, Polysciences, USA) were mixed, allowed to react at room temperature for 20 minutes, and then added to the cells. After 24 hours, the medium was replaced with serum-free DMEM medium, and then the medium was recovered and replaced with fresh medium at 2-day intervals. The recovered medium was subjected to Western blot analysis using secondary antibody (Goat Anti-human IgG, (Fc), Thermo, #31413) to examine antibody expression (FIG. 4). FIG. 4 is a photograph showing the results of Western blot analysis performed to examine whether the antibody was expressed. In FIG. 4, "non-reducing" indicates the results of Western blot analysis performed in a non-reducing condition containing no β-mercaptoethanol, and "reducing" indicates the results of Western blot analysis performed in a reducing condition containing β-mercaptoethanol, and $1^{st}$ to $4^{th}$ indicate the order of each sample obtained while replacing the medium at 48-hr intervals. As can be seen in FIG. 4, in the non-reducing condition, a molecular weight of about 240 kDa was shown, and in the reducing condition, the heavy chain and light chain of the antibody were separated to show an about 55-kDa heavy-chain portion detectable by the secondary antibody, suggesting that the antibody was properly prepared by the above preparation method.

Figure 5:
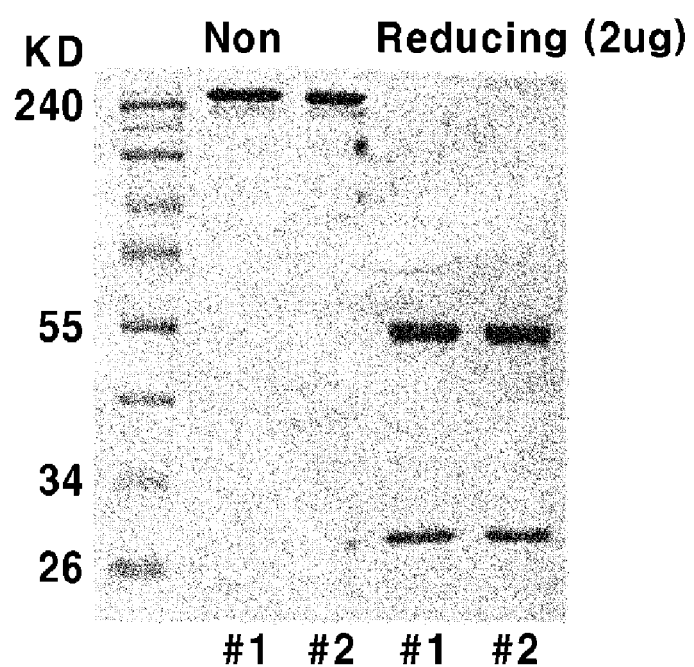
FIG. 5 is a photograph showing the results of electrophoresis of a purified antibody.

The medium confirmed to have the expressed antibody was centrifuged, and then filtered through a 0.22 μm filter (#PR02890 Millipore, USA). A 10 ml column was packed with 400 μl of Protein A Bead (#17-1279-03 GE, Sweden) and washed with PBS, and then about 50 ml of the medium having the expressed C-Met B7 antibody was allowed to pass through the column. The medium was introduced at a flow rate of 0.8 ml/min using a Peri-start pump (Bio-rad, EP-1 Econo-pump). When the medium completely passed through the column, the column was washed with about 100 ml of PBS, and the purified C-Met B7 antibody was recovered with 0.1 M glycine-HCl (#G7126, Sigma, USA). The recovered protein was pH-neutralized with 1M Tris pH 9.0 (#T-1503, Sigma, USA) and dialyzed using PBS, thereby purifying the antibody. The purified antibody was quantified with BCA solution (Thermo, #23228, #1859078) and subjected to SDS-PAGG in order to determine whether or not the antibody was properly purified, had a correct antibody structure and was properly quantified (FIG. 5). FIG. 5 is a photograph showing the results of electrophoresis of the purified antibody. In FIG. 5, "Non" indicates the results of electrophoresis performed in a non-reducing condition containing no β-mercaptoethanol, and "Reducing" indicates the results of electrophoresis performed in a reducing condition containing β-mercaptoethanol, and Reducing indicates, and #1 and #2 indicates the antibodies that resulted from the two purification experiments, respectively. As can be seen in FIG. 5, in the non-reducing condition, a molecular weight of about 240 kDa was shown, and in the reducing condition, the antibody was separated into an about 55 kDa heavy-chain portion and an about 26 kDa light-chain portion, suggesting that the antibody was properly purified by the above purification method.

Example 2

FACS Analysis

Each of Hep3B, HeLa, A549 and HepG2, known to readily express the Met receptor, MCF7 cells known to not readily express the Met receptor, and dog kidney MDCK (Madin-Darby Canine Kidney) cells was prepared, washed twice with PBS, detached by treatment with trypsin, washed again with PBS, and then suspended in PBS (PBA buffer) containing 1% BSA protein. Then, the cells were treated with the purified with the purified B7 antibody at 1:100 at 4° C., after which the cells were washed with PBA buffer and precipitated by centrifugation at 1200 rpm for 3 minutes, and the washing and precipitation process was repeated three times. Then, the resulting B7 antibody was treated for 40 minutes with a 1:200 dilution of secondary fluorescence antibody (Invitrogen, Alexa Fluor 488 goat anti-human IgG, #A11013) that detects human antibody. The cells were washed in the same manner as described above and subjected to FACS analysis (BD Cantoll Flow Cytometer) (FIG. 6). Herein, human IgG (hIgG) was used as the internal standard. FIG. 6 is a graphic diagram showing the results of FACS analysis performed to examine whether the B7 antibody did bind to Hep3B, HeLa, A549, HepG2, MCF7 and dog kidney MDCK cells. As can be seen in FIG. 6, the B7 cell did not bind to the MCF7 cells and dog MDCK cells known to not readily express the Met receptor. This demonstrates that the B7 antibody is a Met receptor-specific humanized antibody.

Example 3

MTT Cell Proliferation Assay

Hep3B cells grown on a 100 mm plate were detached by trypsin, and then seeded into each well of a 96-well plate at a density of 5000 cells/well, and cultured overnight. Next, each well was washed with PBS, and then treated with 40 ng/ml of HGF (R&D, 294-HG-005) and 0.5 μg/ml of B7 antibody in 1% serum-containing MEM medium under various conditions. After 2 days, each well was treated with 200 of MTT solution (Sigma, #M2003) (5 mg/ml) for 2 hours in a 5% $CO_2$ incubator at 37 t, followed by removal of the medium. Then, each well was treated with 100 μl of DMSO (AMRESCO, 0231-500ML). After 5 minutes, the O.D. value at 560 nm was measured using NanoQuant (Tecan, infinite 200) (FIG. 7). Herein, as a negative control, hIgG was used. FIG. 7 is a graphic diagram showing the results of the MTT cell proliferation assay of the Hep3B cells treated with HGF or the B7 antibody. In FIG. 7, Day 0 indicates the day following the cell seeding at which the cells were not treated with anything, and Day 2 indicate a time point at 2 days after treatment with each of the antibodies. As can be seen in FIG. 7, at 2 days after treatment with the B7 antibody, the cells proliferated in the same manner as in the case of treatment with hepatocyte growth factor (HGF) known as the unique ligand of the Met receptor.

Such results suggest that the B7 antibody functions to bind to the Met receptor to promote cell proliferation, like HGF.

Example 4

Wound Healing Assay

The signaling pathway by the interaction between the hepatocyte growth factor and the Met receptor is known to influence cell migration. Thus, a wound healing assay was performed in order to examine whether the B7 antibody influences cell migration.

Example 4-1

Wound Healing Analysis for Hepatocytes

Hep3B cells were seeded into each well of a 6-well plate and incubated to a confluence of 90% or more. Next day, the medium was removed, and the cells were washed with PBS, treated with serum-free MEM medium, and incubated in a $CO_2$ incubator at 37° C. for 24 hours, and then the surface of the cells was evenly wounded with a 200 μl yellow tip. Then, serum-free medium containing either HGF (0.5 nM) known to have a wound healing effect or the B7 antibody (5 nM) was added to the cells, which were then incubated in a $CO_2$ incubator at 37° C. for 18 hours, followed by microscopy (FIG. 8a). FIG. 8a is a photograph showing the influence of the B7 antibody on the healing of the wounded portion of the liver cells. As can be seen in FIG. 8a, the wounded portion was significantly healed when treated with the B7 antibody for 24 hours compared to when not treated with the antibody.

However, when the wound healing effect of treatment with 0.5 nM of HGF was compared with that of treatment with 0.5 nM of the B7 antibody, it was superior to that of treatment with 0.5 nM of the B7 antibody and similar to that of treatment with 5 nM of the B7 antibody, suggesting that the wound healing effect of HGF is about 10 times higher than that of the B7 antibody.

Example 4-2

Wound Healing Assay for Skin Cells

The procedure of Example 4-1 was repeated, except that SK-MEL-28 skin cells were used instead of Hep3B liver cells and were treated with the B7 antibody in a $CO_2$ incubator at 37 for 17 hours. Then, the skin cells were microphotographed (FIG. 8b). FIG. 8b is a photograph showing the influence of the B7 antibody on the healing of the wounded portion of the skin cells. As can be seen in FIG. 8b, the wounded portion was significantly healed when treated with the B7 antibody for 24 hours compared to when not treated with the antibody.

Example 4-3

Wound Healing Assay for Brain Cells

The procedure of Example 4-1 was repeated, except that C6 brain cells were used instead of Hep3B liver cells. Then, the brain cells were microphotographed (FIG. 8c). FIG. 8c is a photograph showing the influence of the B7 antibody on the healing of the wounded portion of the brain cells. As can be seen in FIG. 8c, the wounded portion was significantly healed when treated with the B7 antibody for 24 hours compared to when not treated with the antibody.

The results of Examples 4-1 to 4-3 suggest that the B7 antibody can be used for wound healing.

Example 5

Cell Scattering Assay

Hepatocyte growth factor (HGF) that is the ligand of the Met receptor is also known as a scattering factor and is known to bind to the Met receptor and promote the scattering of cells through a signaling process. Thus, the following experiment was performed whether the B7 antibody shows cell scattering activity, like HGF.

Specifically, one day before treatment with HGF and the B7 antibody, HepG2 cells (10000 cells), A549 cells (10000 cells) and MDCK cells (5000 cells) were seeded into each well of 24-well plate and cultured to adhere to the bottom of each well, followed by washing with PBS. Then, the cells were treated with serum-free medium containing HGF (20 ng/ml) or B7 antibody (1 μg/ml) and incubated for 24 hours, followed by imaging (Canon, Powershot 65015) (FIG. 9).

FIG. 9 is a photograph showing the scattering of HepG2, A549 and MDCK by HGF or the B7 antibody. As can be seen in FIG. 9, when the cells were treated with the B7 antibody, the scattering of A549 and HepG2 cells occurred in the same manner as when the cells were treated with HGF. In addition, there was no observable change in MDCK cells to which the B7 antibody does not bind, as demonstrated by the FACS analysis above. These results indicate that the B7 antibody causes cell scattering that is the typical property of HGF.

The above results demonstrate that the B7 antibody of the present invention can function as an HGF mimmic.

Example 6

Western Blotting

When HGF binds to the Met receptor to cause intracellular signaling, signaling is initiated from auto-phosphorylation of the Met receptor. In order to examine whether the B7 antibody also has this ability, the degree of tyrosine phosphorylation of Met was analyzed by Western blotting.

Specifically, Cos7 cells having the Met receptor overexpressed therein were seeded on a 6-well plate, and when the cells reached a confluence of about 70-80%, the cells were washed with PBS, and then treated with serum-free DMEM medium. After 18 hours, the cells were treated with HGF (20 ng/ml), the B7 antibody (10 μg/ml) or other antibodies (hIgG, C2, F6 or B3) under various conditions. After 15 minutes, the medium was immediately removed, and the cells were washed with cold PBS, kept on ice for 5 minutes, and then treated with RIPA lysis buffer to obtain cell lysates. Each of the lysates was quantified using a BCA kit, and 5× sample buffer was added thereto, followed by boiling for 5 minutes. 40 μg of each sample was loaded and electrophoresed on SDS-PAGE gel and transferred to a nitrocellulose membrane. The membrane was blocked with 4% milk-containing TBST buffer for 1 hour, and then incubated with a 1:200 dilution of Met detection antibody (R&D, AF276) and a 1:500 dilution of phosphorylated Met detection antibody (R&D, #3129) at 4° C. for 18 hours. Next, the membrane was washed with TBST for 5 minutes, and then treated with a 1:5000 dilution of secondary antibody for 1 hour, after which it was washed three times for 7 minutes each washing, and then treated with ECL solution (Intron, West-one, #16033). After 5 minutes, the membrane was photographed in a dark room (FIG. 10).

FIG. 10 is a photograph showing the B7 antibody-mediated increase in the phosphorylation of the Met receptor in the human Met receptor-overexpressed Cos7 cells. As can be seen in FIG. 10, when the cells were treated with the B7 antibody alone, the phosphorylation of Met significantly increased, like when the cells were treated with HGF alone. This suggests that the B7 antibody itself induces various intracellular actions by binding to Met.

Example 7

Immunofluorescence Staining

Hepatocyte growth factor (HGF) is known to induce intracellular endocytosis of the Met receptor. In order to examine whether the B7 antibody induces intracellular endocytosis of the Met receptor, immunostaining and microscopic observation were performed.

Specifically, HeLa cells were detached by trypsin treatment and incubated on an 8-well slide glass (Thermo, #154534). After one day, the cells were treated with HGF (100 ng/ml) or the B7 antibody (1 μg/ml). After 15 minutes, the medium was removed, and the cells were washed with cold PBS. The cells were fixed with 4% paraformaldehyde for 1 hour and washed three times with 0.5% PBST (PBS+ 0.5% Triton-100) for 5 minutes each washing. The cells were blocked with 5% goat serum-containing PBST for 1 hour and treated with a 1:50 dilution of commercial Met receptor detection antibody (R&D, AF276) for 1 hour. Then, the cells were washed three times with 0.5% PBST for 5 minutes each washing and were treated with a 1:200 dilution of fluorescence-labeled secondary antibody (Invitrogen, Alexa Fluor 488 goat anti-human IgG, #A11013) for 1 hour. For nucleus staining, the cells were treated with a 1:1000 dilution of DAPI for 5 minutes and washed three times with PBST in the same manner as described above, after which the cells were treated with fixture solution (Dako, 53023) and covered with cover glass. Then, the cells were stored in a light-shielded place until they were completely hardened. Next, the sample was imaged with a fluorescence microscope (Olympus IX2-UCB) (FIG. 11).

FIG. 11 is a set of fluorescence micrographs showing the B7 antibody-mediated increase in the intracellular internalization of the Met receptor in the HeLa cells. As can be seen in FIG. 11, when the cells were treated with the B7 antibody and stained and the stained Met receptor was observed with the fluorescence microscope, it could be observed that the Met receptor was localized around the cell nucleus, like when the cells were treated with hepatocyte growth factor (HGF). As a result, it is concluded that the B7 antibody that targets the Met receptor binds to the Met receptor so that it induces autophosphorylation of the Met receptor, promotes cell proliferation and migration through the resulting signaling and increases intracellular endocytosis of the Met protein.

Example 8

Surface Plasmon Resonance (SPR) Analysis

In order to measure the direct binding affinity of the B7 antibody for HGF, SPR analysis was performed using ProteOn XPR36 Protein Interaction Array System (BioRad, CA, USA). Specifically, various concentrations (2.5, 5, 10, 20, 40 and 80 nM) of the purified B7 antibody were applied to the flow cell in PBS containing 0.005% Tween 20 at 100 mL/min for 120 seconds and then dissociated for 600 seconds. The obtained values applied to Proteon Manager™ software (ver 2.1) to calculate binding constants. The calculated binding constants were evaluated using a Langmuir 1:1 binding model to calculate the dissociation constant (FIG. 12).

Figure 12:
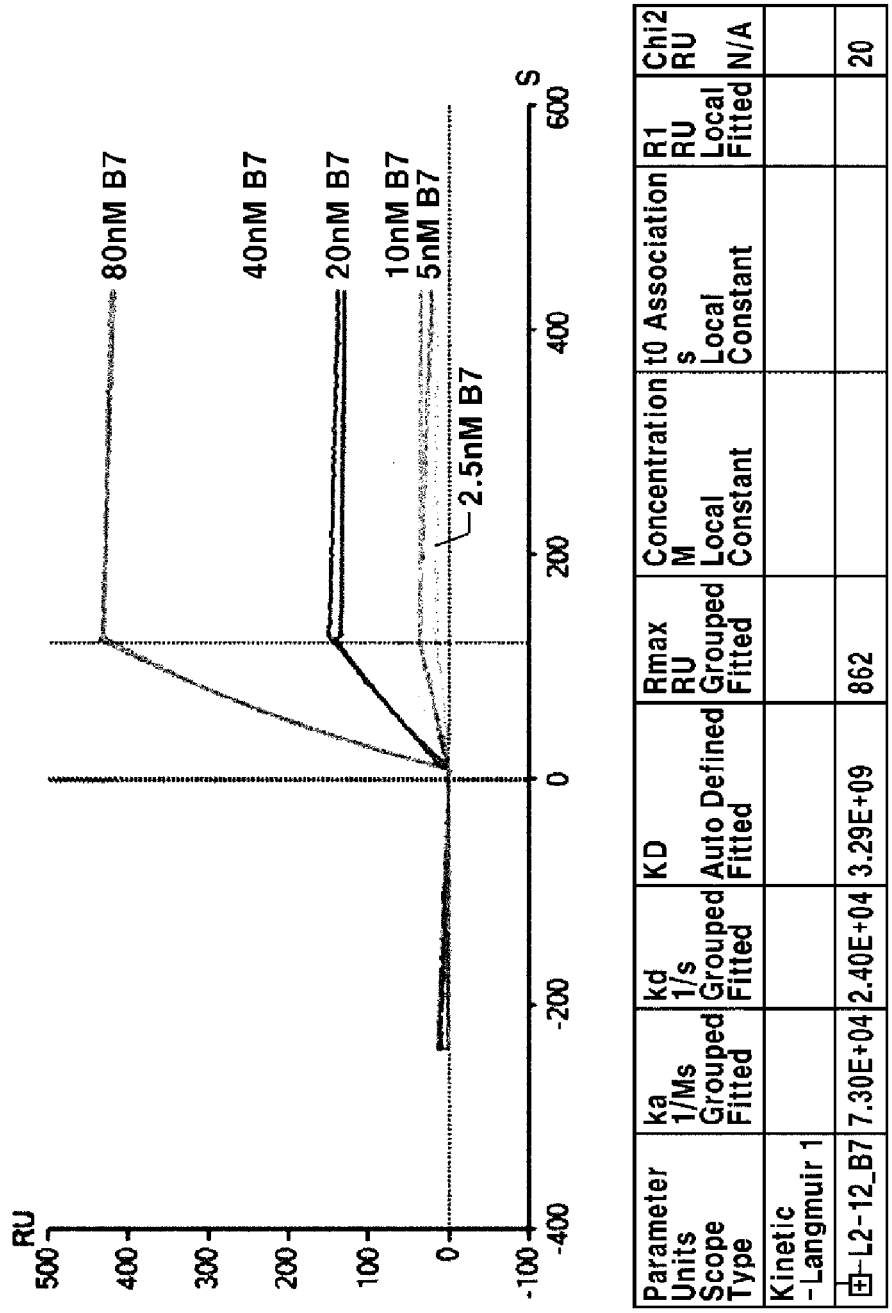
FIG. 12 is a graphic diagram showing a process of calculating the dissociation constant of the B7 antibody by surface plasmon resonance (SPR) analysis.

FIG. 12 is a graphic diagram showing a process of calculating the dissociation constant of the B7 antibody by surface plasmon resonance (SPR) analysis. As can be seen therein, the calculated dissociation constant of the B7 antibody was about 3.3 nM.

Example 9

Comparison of Stabilities of HGF and B7 Antibody in Mouse Plasma 100 ng of HGF was allowed to react with 0.5 μg of Sema-Fc (C-Met extracellular domain Fc fusion protein) at 4° C. for 3 hours. Then, 15 μl of protein A beads were added to each of the B7 antibody (100 ng) and the HGF and allowed to react for 16 hours, followed by precipitation. Then, the supernatant was removed, and the precipitates were washed three times under the conditions of 7,000 rpm and 3 min. Then, 10 μl of mouse plasma was added to each of the precipitates, and the mixture was allowed to react at 37° C. for 4 or 24 hours, after which precipitation, supernatant removal, and washing were performed in the same manner as described above.

5× protein sample buffer was added to each of the washed samples, which were then inactivated by heating. Next, the bead was removed from each sample, and the residue was subjected to SDS-PAGE, followed by Western blot analysis using goat anti-human IgG (Fc) antibody and anti-human HGF antibody (R&D, AF-294-NA) (FIG. 13). FIG. 13 is a Western blot photograph showing the difference in the stabilities of HGF and the B7 antibody in mouse plasma. As can be seen in FIG. 13, the amount of plasma-treated HGF significantly decreased to 1/1000 of that of non-plasma-treated HGF at 4 hours after plasma treatment, but the amount of the plasma-treated B7 antibody did not significantly change compared to that of the non-plasma-treated B7 antibody even at 24 hours after plasma treatment.

Although the results in FIG. 8a indicated that the wound healing effect of the B7 antibody was about 10 times lower than that of HGF, it is expected that the wound healing effect of the B7 antibody in vivo will be significantly superior to that of HGF, because the B7 antibody is not substantially influenced by plasma.

The above-described results suggest that the B7 human antibody of the present invention can function as an HGF mimic that can bind specifically to c-Met. In addition, it can be seen that the stability of B7 antibody in plasma is significantly higher than that of HGF, suggesting that the B7 human antibody can be effectively used as an active ingredient in a wound healing composition.

The invention claimed is:

1. A human antibody comprising: a human complementarity-determining region (CDR) that binds specifically to c-Met; and a framework region (FR), wherein said human antibody comprises a heavy-chain variable region comprising a heavy-chain CDR1 set forth in SEQ ID NO: 1, a heavy-chain CDR2 set forth in SEQ ID NO: 2, and a heavy-chain CDR3 set forth in SEQ ID NO: 3; and a light-chain variable region comprising a light-chain CDR1 set forth in SEQ ID NO: 4, a light-chain CDR2 set forth in SEQ ID NO: 5, and a light-chain CDR3 set forth in SEQ ID NO: 6.

2. The human antibody of claim 1, comprising a heavy-chain variable region amino acid sequence set forth in SEQ ID NO: 7 and a light-chain variable region amino acid sequence set forth in SEQ ID NO: 8.

3. The human antibody of claim 1, wherein the human antibody induces HGF/c-Met signaling.

4. The human antibody of claim 1, wherein the human antibody is a glycosylated and/or PEGylated antibody.

5. The human antibody of claim 4, wherein the antibody has an altered glycosylation and/or PEGylation pattern.

6. A polynucleotide encoding the heavy-chain variable region and light-chain variable region of the human antibody of claim 1.

7. The polynucleotide of claim 6, wherein the polynucleotide encoding the heavy-chain variable region is composed of a nucleotide sequence set forth in SEQ ID NO: 9, and the polynucleotide encoding the light-chain variable region is composed of a nucleotide sequence set forth in SEQ ID NO: 10.

8. An expression vector comprising the polynucleotide of claim 7.

9. A transformant transformed with the expression vector of claim 8.

10. A method for producing a human antibody that binds specifically to c-Met, the method comprising the steps of:
 (i) culturing the transformant of claim 9; and
 (ii) purifying the human antibody comprising: a human complementarity-determining region (CDR) that binds specifically to c-Met; and a framework region (FR) from the culture.

11. A wound healing composition comprising the human antibody of claim 1 as an active ingredient together with a pharmaceutically acceptable carrier.

12. A composition for regenerating cells, the composition comprising the human antibody of claim 1 as an active ingredient together with a pharmaceutically acceptable carrier.

13. The composition of claim 12, wherein the cells are liver cells, neural cells, muscle cells or skin cells.

14. The composition of claim 13, wherein the neural cells are brain cells.

15. The composition of claim 13, wherein the muscular cells are myocardial cells.

16. A composition for treating neurodegenerative disease, the composition comprising the human antibody of claim 1 as an active ingredient together with a pharmaceutically acceptable carrier.

17. The composition of claim 16, wherein the neurodegenerative disease is Parkinson's disease, ischemic disease leading to neuronal infraction, or Alzheimer's disease.

18. A composition for treating ulcerative damage to an organ, the composition comprising the human antibody of claim 1 as an active ingredient together with a pharmaceutically acceptable carrier.

19. The composition of claim 18, wherein the organ is heart, kidney, liver or lung.

20. A drug conjugate comprising a drug linked to the human antibody of claim 1.

* * * * *

SEQUENCE LISTING

<160> NUMBER OF SEQ ID NOS: 46

<210> SEQ ID NO 1
<211> LENGTH: 5
<212> TYPE: PRT
<213> ORGANISM: Artificial Sequence
<220> FEATURE:
<223> OTHER INFORMATION: VH CDR1

<400> SEQUENCE: 1

Gly His Tyr Trp Ser
 1               5

<210> SEQ ID NO 2
<211> LENGTH: 16
<212> TYPE: PRT
<213> ORGANISM: Artificial Sequence
<220> FEATURE:
<223> OTHER INFORMATION: VH CDR2

<400> SEQUENCE: 2

Glu Ile Ser His Ser Gly Asn Thr Asn Tyr Asn Ser Ser Leu Lys Ser
 1               5                  10                  15

<210> SEQ ID NO 3
<211> LENGTH: 13
<212> TYPE: PRT
<213> ORGANISM: Artificial Sequence
<220> FEATURE:
<223> OTHER INFORMATION: VH CDR3

<400> SEQUENCE: 3

Phe Tyr Gly Asp Tyr Pro Ser Ser Tyr Gly Met Asp Val
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: VL CDR1

<400> SEQUENCE: 4

Thr Gly Thr Ile Ser Asp Ile Gly Thr Tyr Asp Phe Val Ser
 1               5                  10

<210> SEQ ID NO 5
<211> LENGTH: 7
<212> TYPE: PRT
<213> ORGANISM: Artificial Sequence
<220> FEATURE:
<223> OTHER INFORMATION: VL CDR2

<400> SEQUENCE: 5

Asp Val Asn Asn Arg Pro Ser
 1               5

<210> SEQ ID NO 6
<211> LENGTH: 13
<212> TYPE: PRT
<213> ORGANISM: Artificial Sequence
<220> FEATURE:
<223> OTHER INFORMATION: VL CDR3

<400> SEQUENCE: 6

Phe Tyr Gly Asp Tyr Pro Ser Ser Tyr Gly Met Asp Val
 1               5                  10

<210> SEQ ID NO 7
<211> LENGTH: 140
<212> TYPE: PRT
<213> ORGANISM: Artificial Sequence
<220> FEATURE:
<223> OTHER INFORMATION: VH

<400> SEQUENCE: 7

```
Met Gly Trp Ser Tyr Ile Ile Leu Phe Leu Val Ala Thr Ala Ala Asp
 1               5                  10                  15

Val His Ser Gln Val Gln Leu Gln Glu Trp Gly Ala Gly Leu Leu Lys
             20                  25                  30

Pro Ser Glu Thr Leu Ser Leu Thr Cys Ala Val Ser Gly Gly Ser Leu
         35                  40                  45

Ser Gly His Tyr Trp Ser Trp Val Arg Leu Pro Pro Gly Lys Gly Leu
     50                  55                  60

Glu Trp Ile Gly Glu Ile Ser His Ser Gly Asn Thr Asn Tyr Asn Ser
 65                  70                  75                  80

Ser Leu Lys Ser Arg Ala Ser Ile Ser Ile Asp Thr Ser Lys Asn Glu
                 85                  90                  95

Tyr Ser Leu Asn Leu Lys Ser Val Thr Ala Val Asp Thr Ala Val Tyr
            100                 105                 110

Tyr Cys Ala Arg Phe Tyr Gly Asp Tyr Pro Ser Ser Tyr Gly Met Asp
        115                 120                 125

Val Trp Gly Gln Gly Thr Thr Val Thr Val Ser Ser
    130                 135                 140
```

<210> SEQ ID NO 8
<211> LENGTH: 132
<212> TYPE: PRT
<213> ORGANISM: Artificial Sequence
<220> FEATURE:
<223> OTHER INFORMATION: VL

<400> SEQUENCE: 8

```
Met Gly Trp Ser Tyr Ile Ile Leu Phe Leu Val Ala Thr Ala Ala Asp
 1               5                  10                  15

Val His Ser Gln Ser Ala Leu Thr Gln Pro Ala Ser Val Ser Gly Ser
             20                  25                  30

Pro Gly Gln Ser Ile Thr Ile Ser Cys Thr Gly Thr Ile Ser Asp Ile
         35                  40                  45

Gly Thr Tyr Asp Phe Val Ser Trp Tyr Gln His Lys Pro Gly Lys Ala
     50                  55                  60

Pro Lys Leu Leu Ile Phe Asp Val Asn Asn Arg Pro Ser Gly Val Ser
 65                  70                  75                  80

Ser Arg Phe Ser Gly Ser Lys Ser Asp Asn Thr Ala Ser Leu Ser Ile
                 85                  90                  95

Ser Gly Phe Gln Ala Glu Asp Glu Ala Asp Tyr Tyr Cys Ser Ser Tyr
            100                 105                 110

Thr Asp Asn Arg Gly Leu Val Leu Phe Gly Gly Gly Thr Lys Leu Thr
        115                 120                 125

Val Leu Arg Ser
    130
```

<210> SEQ ID NO 9
<211> LENGTH: 420
<212> TYPE: DNA

<213> ORGANISM: Artificial Sequence
<220> FEATURE:
<223> OTHER INFORMATION: VH

<400> SEQUENCE: 9

| | | | | | |
|---|---|---|---|---|---|
| atgggatgga | gctatatcat | cctcttttg | gtggccacag | cggccgatgt | ccactcgcag | 60 |
| gtacagctac | aggagtgggg | cgcaggactg | ttgaagcctt | cggagaccct | gtccctcacc | 120 |
| tgcgctgtca | gtggtgggtc | cctcagtggt | cactattgga | gctgggtccg | tctgccccca | 180 |
| gggaaggggc | tggagtggat | tggagaaatc | agtcatagtg | gtaataccaa | ttacaactcg | 240 |
| tccctcaaga | gtcgagcctc | catatccata | gacacgtcca | agaatgagta | ctccttgaac | 300 |
| ctgaagtctg | tgaccgccgt | ggacacggcc | gtgtattact | gtgcgagatt | ctacggtgac | 360 |
| taccctctt | cttacggtat | ggacgtctgg | ggccaaggga | ccacggtcac | cgtctcctca | 420 |

<210> SEQ ID NO 10
<211> LENGTH: 396
<212> TYPE: DNA
<213> ORGANISM: Artificial Sequence
<220> FEATURE:
<223> OTHER INFORMATION: VL

<400> SEQUENCE: 10

| | | | | | |
|---|---|---|---|---|---|
| atgggatgga | gctatatcat | cctcttttg | gtggccacag | cggccgatgt | ccactcgcag | 60 |
| tctgccctga | ctcagcctgc | tccgtgtct | gggtctcctg | gccagtcgat | caccatctcc | 120 |
| tgcactggaa | ccatcagtga | cattggcact | tatgattttg | tctcctggta | ccaacataag | 180 |
| cccggcaagg | cccccaaact | cctgatttt | gatgtcaata | atcggccctc | aggggtttct | 240 |
| agtcgcttct | ctggctccaa | gtctgacaat | acggcctccc | taagcatctc | tggattccag | 300 |
| gctgaagacg | aggctgatta | ctactgcagc | tcatatacag | acaacagagg | ccttgtcctt | 360 |
| ttcggcggag | ggaccaagct | gaccgtccta | agatct | | | 396 |

<210> SEQ ID NO 11
<211> LENGTH: 20
<212> TYPE: DNA
<213> ORGANISM: Artificial Sequence
<220> FEATURE:
<223> OTHER INFORMATION: pYG100-F

<400> SEQUENCE: 11

| | |
|---|---|
| cagctatgac catgattacg | 20 |

<210> SEQ ID NO 12
<211> LENGTH: 20
<212> TYPE: DNA
<213> ORGANISM: Artificial Sequence
<220> FEATURE:
<223> OTHER INFORMATION: pYG100-R

<400> SEQUENCE: 12

| | |
|---|---|
| cttattagcg tttgccatct | 20 |

<210> SEQ ID NO 13
<211> LENGTH: 50
<212> TYPE: DNA
<213> ORGANISM: Artificial Sequence
<220> FEATURE:
<223> OTHER INFORMATION: NATVH4-2

<400> SEQUENCE: 13

| | | |
|---|---|---|
| ttggtggcca cagcggccga tgtccactcg caggtgcagc tacagcagtg | | 50 |

```
<210> SEQ ID NO 14
<211> LENGTH: 26
<212> TYPE: DNA
<213> ORGANISM: Artificial Sequence
<220> FEATURE:
<223> OTHER INFORMATION: NATJH-ALL  Nhe I

<400> SEQUENCE: 14
gaggaggcta gctgaggaga cggtga                                         26

<210> SEQ ID NO 15
<211> LENGTH: 50
<212> TYPE: DNA
<213> ORGANISM: Artificial Sequence
<220> FEATURE:
<223> OTHER INFORMATION: NATVL4

<400> SEQUENCE: 15
ttggtggcca cagcggccga tgtccactcg cagtctgccc tgactcagcc               50

<210> SEQ ID NO 16
<211> LENGTH: 33
<212> TYPE: DNA
<213> ORGANISM: Artificial Sequence
<220> FEATURE:
<223> OTHER INFORMATION: NATJL2-R

<400> SEQUENCE: 16
gaggagagat cttaggacgg tcagcttggt ccc                                 33

<210> SEQ ID NO 17
<211> LENGTH: 12
<212> TYPE: PRT
<213> ORGANISM: Artificial Sequence
<220> FEATURE:
<223> OTHER INFORMATION: VH CDR

<400> SEQUENCE: 17

Asp Val Pro Glu Ala Gly Lys Gly Glu Phe Asp Tyr
 1               5                  10

<210> SEQ ID NO 18
<211> LENGTH: 9
<212> TYPE: PRT
<213> ORGANISM: Artificial Sequence
<220> FEATURE:
<223> OTHER INFORMATION: VH CDR

<400> SEQUENCE: 18

Asp Asp Phe Tyr Asn Gly Thr Leu Asp
 1               5

<210> SEQ ID NO 19
<211> LENGTH: 13
<212> TYPE: PRT
<213> ORGANISM: Artificial Sequence
<220> FEATURE:
<223> OTHER INFORMATION: VH CDR

<400> SEQUENCE: 19

Phe Tyr Gly Asp Tyr Pro Ser Ser Tyr Gly Met Asp Val
 1               5                  10

<210> SEQ ID NO 20
<211> LENGTH: 9
```

```
<212> TYPE: PRT
<213> ORGANISM: Artificial Sequence
<220> FEATURE:
<223> OTHER INFORMATION: VH CDR

<400> SEQUENCE: 20

Gly His Gly Lys Thr Asp Leu Asp Ser
 1               5

<210> SEQ ID NO 21
<211> LENGTH: 15
<212> TYPE: PRT
<213> ORGANISM: Artificial Sequence
<220> FEATURE:
<223> OTHER INFORMATION: VH CDR

<400> SEQUENCE: 21

Asp Leu Gly Arg Glu Ser Arg Arg Trp Val Tyr Tyr Phe Asp Leu
 1               5                  10                  15

<210> SEQ ID NO 22
<211> LENGTH: 17
<212> TYPE: PRT
<213> ORGANISM: Artificial Sequence
<220> FEATURE:
<223> OTHER INFORMATION: VH CDR

<400> SEQUENCE: 22

Ser Lys Pro Val Asp Asp Asp Tyr Val Leu His Tyr Ser Ala Met Glu
 1               5                  10                  15

Val

<210> SEQ ID NO 23
<211> LENGTH: 9
<212> TYPE: PRT
<213> ORGANISM: Artificial Sequence
<220> FEATURE:
<223> OTHER INFORMATION: VH CDR

<400> SEQUENCE: 23

Asp Ser Ala Gly Gly Thr Leu Asp Val
 1               5

<210> SEQ ID NO 24
<211> LENGTH: 5
<212> TYPE: PRT
<213> ORGANISM: Artificial Sequence
<220> FEATURE:
<223> OTHER INFORMATION: VH CDR

<400> SEQUENCE: 24

Gly Arg Asp Leu Arg
 1               5

<210> SEQ ID NO 25
<211> LENGTH: 11
<212> TYPE: PRT
<213> ORGANISM: Artificial Sequence
<220> FEATURE:
<223> OTHER INFORMATION: VH CDR

<400> SEQUENCE: 25

Gly Pro Lys Trp Glu Pro His Ala Phe Asp Val
 1               5                  10

<210> SEQ ID NO 26
```

```
-continued

<211> LENGTH: 11
<212> TYPE: PRT
<213> ORGANISM: Artificial Sequence
<220> FEATURE:
<223> OTHER INFORMATION: VH CDR

<400> SEQUENCE: 26

Ala Asp Val Met Ala Ala Arg Ala Leu Asp Tyr
 1               5                  10

<210> SEQ ID NO 27
<211> LENGTH: 13
<212> TYPE: PRT
<213> ORGANISM: Artificial Sequence
<220> FEATURE:
<223> OTHER INFORMATION: VH CDR
<220> FEATURE:
<221> NAME/KEY: misc_feature
<222> LOCATION: (2)..(3)
<223> OTHER INFORMATION: Xaa = unknown or other

<400> SEQUENCE: 27

Gly Xaa Xaa Arg Ser Ala Lys Arg Ile Ala Phe Asp Leu
 1               5                  10

<210> SEQ ID NO 28
<211> LENGTH: 13
<212> TYPE: PRT
<213> ORGANISM: Artificial Sequence
<220> FEATURE:
<223> OTHER INFORMATION: VH CDR

<400> SEQUENCE: 28

Asn Tyr Asp Ala Ser Arg Thr Trp Asn His Ile Asp Ser
 1               5                  10

<210> SEQ ID NO 29
<211> LENGTH: 9
<212> TYPE: PRT
<213> ORGANISM: Artificial Sequence
<220> FEATURE:
<223> OTHER INFORMATION: VH CDR

<400> SEQUENCE: 29

Trp Ala Arg Asn Tyr Gly Met Asp Val
 1               5

<210> SEQ ID NO 30
<211> LENGTH: 10
<212> TYPE: PRT
<213> ORGANISM: Artificial Sequence
<220> FEATURE:
<223> OTHER INFORMATION: VH CDR

<400> SEQUENCE: 30

Gly Glu Pro Thr Arg Gly Ala Phe Glu Ile
 1               5                  10

<210> SEQ ID NO 31
<211> LENGTH: 7
<212> TYPE: PRT
<213> ORGANISM: Artificial Sequence
<220> FEATURE:
<223> OTHER INFORMATION: VH CDR

<400> SEQUENCE: 31

Gly Gly Arg Met Gly Ser Pro
 1               5
```

<210> SEQ ID NO 32
<211> LENGTH: 11
<212> TYPE: PRT
<213> ORGANISM: Artificial Sequence
<220> FEATURE:
<223> OTHER INFORMATION: Vk CDR

<400> SEQUENCE: 32

Asn Ser Arg Asp Arg Asp Asp Asn His Trp Val
 1               5                   10

<210> SEQ ID NO 33
<211> LENGTH: 10
<212> TYPE: PRT
<213> ORGANISM: Artificial Sequence
<220> FEATURE:
<223> OTHER INFORMATION: Vk CDR

<400> SEQUENCE: 33

Ser Ser Tyr Ala Gly Ser Tyr Thr Ser Val
 1               5                   10

<210> SEQ ID NO 34
<211> LENGTH: 11
<212> TYPE: PRT
<213> ORGANISM: Artificial Sequence
<220> FEATURE:
<223> OTHER INFORMATION: Vk CDR

<400> SEQUENCE: 34

Ser Ser Tyr Thr Asp Asn Arg Gly Leu Val Leu
 1               5                   10

<210> SEQ ID NO 35
<211> LENGTH: 10
<212> TYPE: PRT
<213> ORGANISM: Artificial Sequence
<220> FEATURE:
<223> OTHER INFORMATION: Vk CDR

<400> SEQUENCE: 35

Ser Ser Tyr Thr Ser Ser Ser Thr Leu Ala
 1               5                   10

<210> SEQ ID NO 36
<211> LENGTH: 11
<212> TYPE: PRT
<213> ORGANISM: Artificial Sequence
<220> FEATURE:
<223> OTHER INFORMATION: Vk CDR

<400> SEQUENCE: 36

Gln Ser Tyr Asp Ser Ser Leu Arg Ser Val Val
 1               5                   10

<210> SEQ ID NO 37
<211> LENGTH: 9
<212> TYPE: PRT
<213> ORGANISM: Artificial Sequence
<220> FEATURE:
<223> OTHER INFORMATION: Vk CDR

<400> SEQUENCE: 37

Gln Gln Tyr Gly Ser Ser Pro Leu Thr
 1               5

<210> SEQ ID NO 38
<211> LENGTH: 9
<212> TYPE: PRT
<213> ORGANISM: Artificial Sequence
<220> FEATURE:
<223> OTHER INFORMATION: Vk CDR

<400> SEQUENCE: 38

Gln Glu Ser Asp Arg Ala Leu Tyr Ile
 1               5

<210> SEQ ID NO 39
<211> LENGTH: 9
<212> TYPE: PRT
<213> ORGANISM: Artificial Sequence
<220> FEATURE:
<223> OTHER INFORMATION: Vk CDR

<400> SEQUENCE: 39

Gln Gln Tyr Asp Met Tyr Pro Val Thr
 1               5

<210> SEQ ID NO 40
<211> LENGTH: 9
<212> TYPE: PRT
<213> ORGANISM: Artificial Sequence
<220> FEATURE:
<223> OTHER INFORMATION: Vk CDR

<400> SEQUENCE: 40

Gln Gln Thr Tyr Asp Ser Pro Leu Thr
 1               5

<210> SEQ ID NO 41
<211> LENGTH: 9
<212> TYPE: PRT
<213> ORGANISM: Artificial Sequence
<220> FEATURE:
<223> OTHER INFORMATION: Vk CDR

<400> SEQUENCE: 41

Gln Gln Thr Asp Ser Leu Pro Leu Thr
 1               5

<210> SEQ ID NO 42
<211> LENGTH: 9
<212> TYPE: PRT
<213> ORGANISM: Artificial Sequence
<220> FEATURE:
<223> OTHER INFORMATION: Vk CDR

<400> SEQUENCE: 42

Gln Gln Thr Tyr Ser Phe Pro Arg Thr
 1               5

<210> SEQ ID NO 43
<211> LENGTH: 11
<212> TYPE: PRT
<213> ORGANISM: Artificial Sequence
<220> FEATURE:
<223> OTHER INFORMATION: Vk CDR

<400> SEQUENCE: 43

Gln Ser Tyr Ala Ser Ser Leu Ser Gly Tyr Val
 1               5                   10

```
<210> SEQ ID NO 44
<211> LENGTH: 11
<212> TYPE: PRT
<213> ORGANISM: Artificial Sequence
<220> FEATURE:
<223> OTHER INFORMATION: Vk CDR

<400> SEQUENCE: 44

Gln Ser Tyr Asp Ser Ser Leu Ser Gly Tyr Val
 1               5                  10

<210> SEQ ID NO 45
<211> LENGTH: 12
<212> TYPE: PRT
<213> ORGANISM: Artificial Sequence
<220> FEATURE:
<223> OTHER INFORMATION: Vk CDR

<400> SEQUENCE: 45

Val Gly Thr Trp Asp Ala Ser Leu Ser Thr Gly Leu
 1               5                  10

<210> SEQ ID NO 46
<211> LENGTH: 11
<212> TYPE: PRT
<213> ORGANISM: Artificial Sequence
<220> FEATURE:
<223> OTHER INFORMATION: Vk CDR
<220> FEATURE:
<221> NAME/KEY: misc_feature
<222> LOCATION: (6)..(7)
<223> OTHER INFORMATION: Xaa = unknown or other

<400> SEQUENCE: 46

Gln Gln Ala Asn Ser Xaa Xaa Phe Pro Leu Thr
 1               5                  10
```